US009498619B2

(12) United States Patent
Goode et al.

(10) Patent No.: US 9,498,619 B2
(45) Date of Patent: Nov. 22, 2016

(54) IMPLANTABLE ELECTRICAL STIMULATION LEADS

(71) Applicant: EndoStim, Inc., St. Louis, MO (US)

(72) Inventors: Paul V. Goode, Round Rock, TX (US); Ofer Glasberg, Zichron Ya'akov (IL); Virender K. Sharma, Paradise Valley, AZ (US)

(73) Assignee: EndoStim, Inc., St. Louis, MO (US)

( * ) Notice: Subject to any disclaimer, the term of this patent is extended or adjusted under 35 U.S.C. 154(b) by 205 days.

(21) Appl. No.: 14/191,085

(22) Filed: Feb. 26, 2014

(65) Prior Publication Data
US 2014/0243593 A1 Aug. 28, 2014

Related U.S. Application Data

(60) Provisional application No. 61/769,732, filed on Feb. 26, 2013.

(51) Int. Cl.
*A61N 1/05* (2006.01)
*A61B 1/018* (2006.01)
(Continued)

(52) U.S. Cl.
CPC ........... *A61N 1/0509* (2013.01); *A61F 5/0026* (2013.01); *A61B 1/00082* (2013.01); *A61B 1/00087* (2013.01); *A61B 2017/0034* (2013.01); *A61N 1/36007* (2013.01)

(58) Field of Classification Search
CPC .......... A61B 1/00082; A61B 1/00087; A61B 18/1442; A61B 18/1445; A61B 2017/00292; A61B 2017/00296; A61B 2017/0034; A61N 1/0507; A61N 1/0509; A61N 1/36007
USPC ....................................... 606/48, 51; 607/40
See application file for complete search history.

(56) References Cited

U.S. PATENT DOCUMENTS

| 3,909,883 A | 10/1975 | Fegen |
| 3,910,281 A | 10/1975 | Kletschka |

(Continued)

FOREIGN PATENT DOCUMENTS

| CN | 1476339 | 2/2004 |
| CN | 1494451 A | 5/2004 |

(Continued)

OTHER PUBLICATIONS

Christensen et al., 'Physiologic Specialization at Esophagogastric Junction in Three Species' , American Journal of Physiology, vol. 225, No. 6, Dec. 1973, 1265-1270.

(Continued)

*Primary Examiner* — John P Leubecker
(74) *Attorney, Agent, or Firm* — Novel IP

(57) ABSTRACT

An implantable electrical stimulation lead for the treatment of biological conditions includes a lead body with an electrical connector at one end and a pair of monopolar branches at the other end. The lead body has a length ranging from 390 mm to 490 mm to allow for implantation from an incision site further removed from the final positioning site of the electrodes. The branches have lengths ranging from 50 mm to 120 mm for the both branches. These lengths facilitate successful laparoscopic implantation at sites with confined anatomy, such as, near the gastroesophageal junction. The branches include needles and sutures at their ends for suturing anchors positioned on the branches to surrounding tissue. The needles have curves designed to facilitate maneuvering in confined anatomy. A separate lead includes a suture loop connecting the ends of the first and second branches rather than needles. The loop is used to pull the lead through the working channel of an endoscope. The anchors on the lead are porous and allow for the ingrowth of surrounding tissue for fixing the branches in place.

15 Claims, 9 Drawing Sheets

(51) Int. Cl.
*A61F 5/00* (2006.01)
*A61N 1/36* (2006.01)
*A61B 17/00* (2006.01)
*A61B 1/00* (2006.01)

(56) References Cited

U.S. PATENT DOCUMENTS

| | | | |
|---|---|---|---|
| 4,393,883 A * | 7/1983 | Smyth | A61N 1/056 607/123 |
| 4,414,986 A | 11/1983 | Dickhudt | |
| 4,612,934 A | 9/1986 | Borkan | |
| 4,735,205 A * | 4/1988 | Chachques | A61N 1/36003 607/2 |
| 5,117,827 A | 6/1992 | Stuebe | |
| 5,188,104 A | 2/1993 | Wernicke | |
| 5,193,539 A | 3/1993 | Schulman | |
| 5,197,491 A | 3/1993 | Anderson | |
| 5,231,988 A | 8/1993 | Wernicke | |
| 5,263,480 A | 11/1993 | Wernicke | |
| 5,292,344 A | 3/1994 | Douglas | |
| 5,360,428 A * | 11/1994 | Hutchinson, Jr. | A61B 18/1482 606/41 |
| 5,423,872 A | 6/1995 | Cigaina | |
| 5,531,778 A * | 7/1996 | Maschino | A61N 1/0556 600/396 |
| 5,540,730 A | 7/1996 | Terry | |
| 5,556,425 A | 9/1996 | Hewson | |
| 5,649,902 A | 7/1997 | Yoon | |
| 5,674,205 A | 10/1997 | Pasricha | |
| 5,690,691 A | 11/1997 | Chen | |
| 5,697,375 A | 12/1997 | Hickey | |
| 5,709,224 A * | 1/1998 | Behl | A61B 18/1492 128/898 |
| 5,716,385 A | 2/1998 | Mittal | |
| 5,716,392 A | 2/1998 | Bourgeois | |
| 5,810,810 A * | 9/1998 | Tay | A61B 17/0057 606/50 |
| 5,836,994 A | 11/1998 | Bourgeois | |
| 5,861,014 A | 1/1999 | Familoni | |
| 5,861,044 A | 1/1999 | Crenshaw | |
| 5,882,340 A | 3/1999 | Yoon | |
| 5,893,883 A | 4/1999 | Torgerson | |
| 5,935,126 A | 8/1999 | Riza | |
| 5,995,872 A | 11/1999 | Bourgeois | |
| 6,006,755 A | 12/1999 | Edwards | |
| 6,026,326 A | 2/2000 | Bardy | |
| 6,041,258 A | 3/2000 | Cigaina | |
| 6,051,017 A | 4/2000 | Loeb | |
| 6,091,992 A | 7/2000 | Bourgeois | |
| 6,097,984 A | 8/2000 | Douglas | |
| 6,216,039 B1 | 4/2001 | Bourgeois | |
| 6,221,039 B1 * | 4/2001 | Durgin | A61B 18/1492 604/22 |
| 6,243,607 B1 | 6/2001 | Mintchev | |
| 6,254,598 B1 | 7/2001 | Edwards | |
| 6,285,897 B1 | 9/2001 | Kilcoyne | |
| 6,321,124 B1 | 11/2001 | Cigaina | |
| 6,360,130 B1 * | 3/2002 | Duysens | A61N 1/0587 607/119 |
| 6,381,495 B1 | 4/2002 | Jenkins | |
| 6,449,511 B1 | 9/2002 | Mintchev | |
| 6,510,332 B1 | 1/2003 | Greenstein | |
| 6,542,776 B1 | 4/2003 | Gordon | |
| 6,571,127 B1 | 5/2003 | Ben-Haim | |
| 6,587,719 B1 | 7/2003 | Barrett | |
| 6,591,137 B1 | 7/2003 | Fischell | |
| 6,611,715 B1 | 8/2003 | Boveja | |
| 6,612,983 B1 | 9/2003 | Marchal | |
| 6,615,084 B1 | 9/2003 | Cigaina | |
| 6,678,561 B2 | 1/2004 | Forsell | |
| 6,684,104 B2 | 1/2004 | Gordon | |
| 6,749,607 B2 | 6/2004 | Edwards | |
| 6,754,536 B2 | 6/2004 | Swoyer | |
| 6,760,626 B1 | 7/2004 | Boveja | |
| 6,826,428 B1 | 11/2004 | Chen | |
| 6,832,114 B1 | 12/2004 | Whitehurst | |
| 6,853,862 B1 | 2/2005 | Marchal | |
| 6,876,885 B2 | 4/2005 | Swoyer | |
| 6,879,859 B1 | 4/2005 | Boveja | |
| 6,879,861 B2 | 4/2005 | Benz | |
| 6,901,295 B2 | 5/2005 | Sharma | |
| 6,915,165 B2 | 7/2005 | Forsell | |
| 6,947,792 B2 | 9/2005 | Ben-Haim | |
| 6,952,613 B2 | 10/2005 | Swoyer | |
| 7,006,871 B1 | 2/2006 | Darvish | |
| 7,016,735 B2 | 3/2006 | Imran | |
| 7,054,689 B1 | 5/2006 | Whitehurst | |
| 7,054,690 B2 | 5/2006 | Imran | |
| 7,076,305 B2 | 7/2006 | Imran | |
| 7,076,306 B2 | 7/2006 | Marchal | |
| 7,087,053 B2 | 8/2006 | Vanney | |
| 7,114,502 B2 | 10/2006 | Schulman | |
| 7,120,498 B2 | 10/2006 | Imran | |
| 7,146,216 B2 | 12/2006 | Bumm | |
| 7,167,750 B2 | 1/2007 | Knudson | |
| 7,177,693 B2 | 2/2007 | Starkebaum | |
| 7,200,443 B2 | 4/2007 | Faul | |
| 7,203,551 B2 | 4/2007 | Houben | |
| 7,263,405 B2 | 8/2007 | Boveja | |
| 7,299,091 B2 | 11/2007 | Barrett | |
| 7,310,557 B2 | 12/2007 | Maschino | |
| 7,340,306 B2 | 3/2008 | Barrett | |
| 7,343,201 B2 | 3/2008 | Mintchev | |
| 7,363,084 B2 | 4/2008 | Kurokawa | |
| 7,444,183 B2 | 10/2008 | Knudson | |
| 7,477,994 B2 | 1/2009 | Sunshine | |
| 7,519,431 B2 | 4/2009 | Goetz | |
| 7,519,433 B2 | 4/2009 | Foley | |
| 7,558,629 B2 | 7/2009 | Keimel | |
| 7,593,777 B2 | 9/2009 | Gerber | |
| 7,599,736 B2 | 10/2009 | DiLorenzo | |
| 7,620,454 B2 | 11/2009 | Dinsmoor | |
| 7,664,551 B2 | 2/2010 | Cigaina | |
| 7,676,270 B2 | 3/2010 | Imran | |
| 7,702,395 B2 | 4/2010 | Towe | |
| 7,702,934 B2 | 4/2010 | Watanabe | |
| 7,711,437 B1 | 5/2010 | Bornzin | |
| 7,720,539 B2 | 5/2010 | Mintchev | |
| 7,729,771 B2 | 6/2010 | Knudson | |
| 7,734,355 B2 | 6/2010 | Cohen | |
| 7,738,961 B2 | 6/2010 | Sharma | |
| 7,742,818 B2 | 6/2010 | Dinsmoor | |
| 7,794,425 B2 | 9/2010 | Gobel | |
| 7,813,809 B2 | 10/2010 | Strother | |
| 7,835,796 B2 | 11/2010 | Maschino | |
| 7,848,802 B2 | 12/2010 | Goetz | |
| 7,899,540 B2 | 3/2011 | Maschino | |
| 7,914,468 B2 | 3/2011 | Shalon | |
| 7,941,221 B2 | 5/2011 | Foley | |
| 7,957,807 B2 | 6/2011 | Starkebaum | |
| 7,962,214 B2 | 6/2011 | Byerman | |
| 7,983,755 B2 | 7/2011 | Starkebaum | |
| 8,135,470 B2 | 3/2012 | Keimel | |
| 8,155,758 B2 | 4/2012 | Roline | |
| 8,160,709 B2 | 4/2012 | Soffer | |
| 8,185,206 B2 | 5/2012 | Starkebaum | |
| 8,282,561 B2 | 10/2012 | Towe | |
| 8,380,321 B2 | 2/2013 | Goetz | |
| 8,406,868 B2 | 3/2013 | Buschman | |
| 8,423,134 B2 | 4/2013 | Buschman | |
| 8,447,403 B2 | 5/2013 | Sharma | |
| 8,447,404 B2 | 5/2013 | Sharma | |
| 8,452,407 B2 | 5/2013 | Whitehurst | |
| 8,467,874 B2 | 6/2013 | Chen | |
| 8,467,884 B2 | 6/2013 | Chen | |
| 8,521,292 B2 | 8/2013 | Wei | |
| 8,538,532 B2 | 9/2013 | Starkebaum | |
| 8,538,534 B2 | 9/2013 | Soffer | |
| 8,543,210 B2 | 9/2013 | Sharma | |
| 8,556,952 B2 | 10/2013 | Shadduck | |
| 8,594,811 B2 | 11/2013 | Chen | |
| 8,712,529 B2 | 4/2014 | Sharma | |
| 8,712,530 B2 | 4/2014 | Sharma | |
| 8,761,903 B2 | 6/2014 | Chen | |

(56) References Cited

U.S. PATENT DOCUMENTS

| | | |
|---|---|---|
| 8,792,986 B2 | 7/2014 | Cigaina |
| 8,831,737 B2 | 9/2014 | Wesselink |
| 8,892,217 B2 | 11/2014 | Camps |
| 9,020,597 B2 | 4/2015 | Sharma |
| 9,061,147 B2 | 6/2015 | Sharma |
| 2001/0041831 A1 | 11/2001 | Starkweather |
| 2002/0103522 A1* | 8/2002 | Swoyer ............ A61N 1/05 607/116 |
| 2002/0138075 A1 | 9/2002 | Edwards |
| 2002/0161414 A1 | 10/2002 | Flesler |
| 2002/0165589 A1 | 11/2002 | Imran |
| 2003/0014086 A1 | 1/2003 | Sharma |
| 2003/0028226 A1 | 2/2003 | Thompson |
| 2003/0055463 A1* | 3/2003 | Gordon ............ A61N 1/05 607/40 |
| 2003/0078633 A1 | 4/2003 | Firlik |
| 2003/0120321 A1 | 6/2003 | Bumm |
| 2003/0144708 A1 | 7/2003 | Starkebaum |
| 2003/0195600 A1 | 10/2003 | Tronnes |
| 2004/0012088 A1 | 1/2004 | Fukasawa |
| 2004/0015201 A1 | 1/2004 | Greenstein |
| 2004/0024428 A1 | 2/2004 | Barrett |
| 2004/0039427 A1 | 2/2004 | Barrett |
| 2004/0044376 A1 | 3/2004 | Flesler |
| 2004/0059393 A1 | 3/2004 | Policker |
| 2004/0073453 A1 | 4/2004 | Nenov |
| 2004/0088033 A1 | 5/2004 | Smits |
| 2004/0116977 A1 | 6/2004 | Finch |
| 2004/0138586 A1 | 7/2004 | Ganz |
| 2004/0147976 A1 | 7/2004 | Gordon |
| 2004/0167583 A1 | 8/2004 | Knudson |
| 2004/0172088 A1 | 9/2004 | Knudson |
| 2004/0186544 A1 | 9/2004 | King |
| 2004/0193229 A1 | 9/2004 | Starkebaum |
| 2004/0243182 A1 | 12/2004 | Cohen |
| 2005/0027328 A1 | 2/2005 | Greenstein |
| 2005/0049655 A1 | 3/2005 | Boveja |
| 2005/0065571 A1 | 3/2005 | Imran |
| 2005/0070974 A1 | 3/2005 | Knudson |
| 2005/0075678 A1 | 4/2005 | Faul |
| 2005/0090873 A1 | 4/2005 | Imran |
| 2005/0131486 A1 | 6/2005 | Boveja |
| 2005/0137480 A1 | 6/2005 | Alt |
| 2005/0137643 A1 | 6/2005 | Mintchev |
| 2005/0137644 A1 | 6/2005 | Boveja |
| 2005/0143787 A1 | 6/2005 | Boveja |
| 2005/0149141 A1 | 7/2005 | Starkebaum |
| 2005/0149142 A1 | 7/2005 | Starkebaum |
| 2005/0149146 A1 | 7/2005 | Boveja |
| 2005/0222637 A1 | 10/2005 | Chen |
| 2005/0222638 A1 | 10/2005 | Foley |
| 2005/0245788 A1 | 11/2005 | Gerber |
| 2005/0251219 A1 | 11/2005 | Evans |
| 2006/0004304 A1 | 1/2006 | Parks |
| 2006/0015162 A1 | 1/2006 | Edward |
| 2006/0036293 A1 | 2/2006 | Whitehurst |
| 2006/0064037 A1 | 3/2006 | Shalon |
| 2006/0074459 A1 | 4/2006 | Flesler |
| 2006/0095077 A1 | 5/2006 | Tronnes |
| 2006/0106442 A1 | 5/2006 | Richardson |
| 2006/0116736 A1 | 6/2006 | DiLorenzo |
| 2006/0167498 A1 | 7/2006 | DiLorenzo |
| 2006/0200217 A1 | 9/2006 | Wessman |
| 2006/0206160 A1 | 9/2006 | Cigaina |
| 2006/0218011 A1 | 9/2006 | Walker |
| 2006/0247717 A1 | 11/2006 | Starkebaum |
| 2006/0247718 A1 | 11/2006 | Starkebaum |
| 2006/0247722 A1 | 11/2006 | Maschino |
| 2006/0265021 A1 | 11/2006 | Herbert |
| 2007/0016274 A1 | 1/2007 | Boveja |
| 2007/0049793 A1 | 3/2007 | Ignagni |
| 2007/0060955 A1 | 3/2007 | Strother |
| 2007/0060968 A1 | 3/2007 | Strother |
| 2007/0060979 A1 | 3/2007 | Strother |
| 2007/0066995 A1 | 3/2007 | Strother |
| 2007/0067000 A1 | 3/2007 | Strother |
| 2007/0100388 A1 | 5/2007 | Gerber |
| 2007/0106337 A1 | 5/2007 | Errico |
| 2007/0106338 A1 | 5/2007 | Errico |
| 2007/0142699 A1 | 6/2007 | Jandrall |
| 2007/0142831 A1 | 6/2007 | Shadduck |
| 2007/0142884 A1 | 6/2007 | Jandrall |
| 2007/0156182 A1 | 7/2007 | Castel |
| 2007/0162084 A1 | 7/2007 | Chen |
| 2007/0162085 A1 | 7/2007 | DiLorenzo |
| 2007/0179542 A1 | 8/2007 | Prakash |
| 2007/0238942 A1 | 10/2007 | Baylor |
| 2007/0239248 A1 | 10/2007 | Hastings |
| 2007/0244375 A1 | 10/2007 | Jenkins |
| 2007/0255118 A1 | 11/2007 | Miesel |
| 2007/0255335 A1 | 11/2007 | Herbert |
| 2007/0255336 A1 | 11/2007 | Herbert |
| 2007/0255352 A1 | 11/2007 | Roline |
| 2007/0265662 A1 | 11/2007 | Ufford |
| 2007/0265666 A1 | 11/2007 | Roberts |
| 2007/0265668 A1 | 11/2007 | Reinke |
| 2007/0265671 A1 | 11/2007 | Roberts |
| 2007/0265674 A1 | 11/2007 | Olson |
| 2007/0282410 A1 | 12/2007 | Cross |
| 2008/0021512 A1 | 1/2008 | Knudson |
| 2008/0039904 A1 | 2/2008 | Bulkes |
| 2008/0046062 A1* | 2/2008 | Camps ............ A61N 1/05 607/133 |
| 2008/0058836 A1* | 3/2008 | Moll ............ A61B 1/00082 606/130 |
| 2008/0058891 A1 | 3/2008 | Ben-Haim |
| 2008/0086179 A1 | 4/2008 | Sharma |
| 2008/0132968 A1 | 6/2008 | Starkebaum |
| 2008/0147137 A1 | 6/2008 | Cohen |
| 2008/0154191 A1 | 6/2008 | Gobel |
| 2008/0183238 A1 | 7/2008 | Chen |
| 2008/0195171 A1 | 8/2008 | Sharma |
| 2008/0208355 A1 | 8/2008 | Stack |
| 2009/0012421 A1 | 1/2009 | Bek |
| 2009/0018617 A1 | 1/2009 | Skelton |
| 2009/0018619 A1 | 1/2009 | Skelton |
| 2009/0020406 A1 | 1/2009 | Nirmalakhandan |
| 2009/0030475 A1 | 1/2009 | Brynelsen |
| 2009/0069803 A1 | 3/2009 | Starkebaum |
| 2009/0076498 A1* | 3/2009 | Saadat ............ A61B 18/1492 606/41 |
| 2009/0088817 A1 | 4/2009 | Starkebaum |
| 2009/0131993 A1 | 5/2009 | Rousso |
| 2009/0132001 A1 | 5/2009 | Soffer |
| 2009/0187223 A1 | 7/2009 | Gross |
| 2009/0204063 A1 | 8/2009 | Policker |
| 2009/0264951 A1 | 10/2009 | Sharma |
| 2009/0281553 A1 | 11/2009 | Kalloo |
| 2010/0004648 A1 | 1/2010 | Edwards |
| 2010/0049026 A1 | 2/2010 | Gerber |
| 2010/0057085 A1* | 3/2010 | Holcomb ............ A61B 18/1445 606/51 |
| 2010/0069789 A1* | 3/2010 | Hirota ............ A61B 17/3401 600/567 |
| 2010/0170812 A1* | 7/2010 | Odierno ............ A61B 17/06061 206/63.3 |
| 2010/0198039 A1 | 8/2010 | Towe |
| 2010/0324432 A1 | 12/2010 | Bjoerling |
| 2011/0004266 A1 | 1/2011 | Sharma |
| 2011/0046653 A1 | 2/2011 | Addington |
| 2011/0071589 A1 | 3/2011 | Starkebaum |
| 2011/0213437 A9 | 9/2011 | Armstrong |
| 2011/0224665 A1 | 9/2011 | Crosby |
| 2011/0295335 A1 | 12/2011 | Sharma |
| 2011/0295336 A1 | 12/2011 | Sharma |
| 2011/0307027 A1 | 12/2011 | Sharma |
| 2011/0307028 A1 | 12/2011 | Sharma |
| 2012/0232610 A1 | 9/2012 | Soffer |
| 2012/0259389 A1 | 10/2012 | Starkebaum |
| 2012/0265103 A1 | 10/2012 | Policker |
| 2012/0277619 A1 | 11/2012 | Starkebaum |
| 2013/0030503 A1* | 1/2013 | Yaniv ............ A61N 1/36007 607/62 |
| 2013/0035740 A1 | 2/2013 | Sharma |

(56) References Cited

U.S. PATENT DOCUMENTS

| | | |
|---|---|---|
| 2013/0072928 A1 | 3/2013 | Schaer |
| 2013/0090551 A1 | 4/2013 | Sharma |
| 2013/0178912 A1 | 7/2013 | Sharma |
| 2013/0218229 A1 | 8/2013 | Sharma |
| 2013/0231660 A1 | 9/2013 | Edwards |
| 2013/0238048 A1* | 9/2013 | Almendinger ....... A61N 1/0509 607/40 |
| 2014/0012348 A1 | 1/2014 | Starkebaum |
| 2014/0018657 A1 | 1/2014 | Sharma |
| 2014/0088664 A1 | 3/2014 | Sharma |
| 2014/0088666 A1 | 3/2014 | Goetz |
| 2014/0135886 A1 | 5/2014 | Cook |
| 2014/0222106 A1 | 8/2014 | Sharma |
| 2014/0228911 A1 | 8/2014 | Sharma |
| 2014/0243593 A1 | 8/2014 | Goode |
| 2015/0045786 A1 | 2/2015 | Edwards |
| 2015/0119952 A1 | 4/2015 | Sharma |
| 2016/0001071 A1 | 1/2016 | Sharma |

FOREIGN PATENT DOCUMENTS

| | | |
|---|---|---|
| CN | 102725021 | 10/2012 |
| EP | 1004330 | 5/2000 |
| WO | 9853878 | 12/1998 |
| WO | 9903532 | 1/1999 |
| WO | 9930776 | 6/1999 |
| WO | 0061223 | 10/2000 |
| WO | 0061223 A1 | 10/2000 |
| WO | 0061224 | 10/2000 |
| WO | 0061224 A1 | 10/2000 |
| WO | 0243467 | 6/2002 |
| WO | 0243467 A2 | 6/2002 |
| WO | 02089655 | 11/2002 |
| WO | 2005051486 A1 | 9/2005 |
| WO | 2007137026 | 11/2007 |
| WO | 2009009276 | 1/2009 |
| WO | 2009114008 A1 | 9/2009 |
| WO | 2010027963 | 3/2010 |
| WO | 2010135634 | 11/2010 |
| WO | 2012151449 | 11/2012 |
| WO | 2014032030 | 2/2014 |
| WO | 2015034867 | 3/2015 |
| WO | 2015077425 | 5/2015 |
| WO | 2015077435 | 5/2015 |

OTHER PUBLICATIONS

Ellis, et al., 'The Prevention of Experimentally Induced Reflux by Electrical Stimulation of the Distal Esophagus', American Journal of Surgery, vol. 115, Apr. 1968, 482-487.

Gonzalez et al., 'Different Responsiveness of Excitatory and Inhibitory Enteric Motor Neurons in the Human Esophagus to Electrical Field Stimulation and to Nicotine', Am J Physiol Gastrointest Liver Physiol, 287:G299-G306, 2004.

Kahrilas et al., 'Impact of Fundoplication on Bolus Transit Across Esophagogastric Junction', American Physiological Society, 1998, 1386-1393.

Kamath et al., 'Neurocardiac and Cerebral Responses Evoked by Esophageal Vago-Afferent Stimulation in Humans: Effects of Varying Intensities', Cardiovascular Research, 40 (1998) 591-599.

Lund et al., 'Electrical Stimulation of Esophageal Smooth Muscle and Effects of Antagonists', American Journal of Physiology, vol. 217, No. 5, Nov. 1969, 1369-1374.

Stein et al., 'Three-dimensional Imaging of the Lower Esophageal Sphincter in Gastroesophageal Reflux Disease,' Annual Meeting of the American Surgical Association, Apr. 11-13, 1991, 374-383.

International Search Report for PCT/US2007/068907, Aug. 7, 2008.

International Search Report for PCT/US2012/036408, Aug. 17, 2012.

Summary of Neurostimulation Systems Features, Advanced Neuromodulation Systems (ANS) home page, accessed on May 31, 2007 at http://web.archive.org/web/20040211224857/www.ans-medical.com/patients/WhichSystemIsBest/SumOfNeurostimulation.html.

International Search Report for PCT/US2008/053780, Jun. 8, 2009.

International Search Report for PCT/US2008/056479, Aug. 20, 2008.

International Search Report for PCT/US2011/027243, Jul. 8, 2011.

International Search Report for PCT/US12/053576, Dec. 24, 2012.

International Search Report for PCT/US2012/033695, Aug. 7, 2012.

EPO Search Report EP09704463, Jan. 10, 2011, Virender K. Sharma.

International Search Report for PCT/US2013/056520, Apr. 4, 2014.

Clarke et al., 'An endoscopically implantable device stimulates the lower esophageal sphincter on demand by remote control: a study using a canine model', Endoscopy 2007; 39: 72-76.

Xing et al., 'Gastric Electrical Stimulation Significantly Increases Canine Lower Esophageal Pressure' M1811 Cleveland, OH.

Office Action dated Jun. 8, 2016 for U.S. Appl. No. 14/475,736.

Office Action dated Mar. 15, 2016 for U.S. Appl. No. 14/695,267.

Office Action dated Mar. 17, 2016 for U.S. Appl. No. 14/500,856.

Office Action dated May 20, 2016 for U.S. Appl. No. 13/975,162.

Office Action dated May 4, 2016 for U.S. Appl. No. 14/548,793.

Office Action dated Jun. 19, 2015 for U.S. Appl. No. 13/975,162.

Xing et al., 'Gastric Electrical Stimulation Significantly Increases Canine Lower Esophageal Pressure' Gastroenterology 122: May Issue, A579, 2003. Presented as a poster at Digestive Disease Week in Orlando, FL on Monday, May 19, 2003.

Xing et al, 'Gastric Electrical Stimulation (GES) with Parameters for Morbid Obesity Elevates Lower Esophageal Sphincter (LES) Pressure in Conscious Dogs'; Obesity Surgery; 15; 2005; pp. 1321-1327.

Cigaina, Valerio; Long-term Follow-Up of Gastric Stimulation for Obesity: The Mestre 8-Year Experience; Obesity Surgery; 14; 2004; S14-22.

Xing et al, 'Gastric Electrical Stimulation Significantly Increases Canine Lower Esophageal Sphincter Pressure'; Digestive Diseases and Sciences; vol. 50, No. 8 (Aug. 2005), pp. 1481-1487.

Sanmiguel et al, 'Effect of electrical stimulation of the LES on LES pressure in a canine model'; Am J Physiol Gastrointest Live Physiol; 295: 389-394; 2008.

Clarke et al,. 'An Endoscopic Implantable Device Stimulates the LES On-Demand by Remote Control in a Canine Model'; Gastrointestinal Endoscopy, vol. 63, No. 5; 2006, AB103, 759.

Kantsevoy et al., 'An Endoscopically Implantable On-Demand Stimulator Is Successful in Increasing Lower Esophageal Sphincter Pressure in a Porcine Model'; Gastrointestinal Endoscopy, vol. 61, No. 5: 2005, AB79, 222.

Sallam et al, 'Feasibility of gastric electrical stimulation by percutaneous endoscopic transgastric electrodes'; Gastrointestinal Endoscopy; vol. 68, No. 4; 2008, 754-759.

Notice of Allowance dated Feb. 20, 2015 for U.S. Appl. No. 14/201,645.

Office Action dated Feb. 20, 2015 for U.S. Appl. No. 14/175,927.

First Office Action for Application No. CN 01819456, dated Nov. 18, 2014.

Office Action dated Apr. 11, 2014 for U.S. Appl. No. 13/602,184.

Notice of Allowance dated Jul. 21, 2014 for U.S. Appl. No. 13/447,168.

Notice of Allowance dated Apr. 3, 2014 for U.S. Appl. No. 13/447,168.

Notice of Allowance dated Mar. 17, 2014 for U.S. Appl. No. 13/447,168.

Office Action dated Jul. 8, 2014 for U.S. Appl. No. 13/463,803.

Shellock, Frank G. 'RF Bion Microstimulator' MRISafety.com, http://www.mrisafety.com/SafetyInfov.asp?SafetyInfoID=254, Shellock R & D Services, Inc. and Frank G. Shellock, Ph.D., 4 pages, 2014.

Notice of Allowance dated Dec. 24, 2014 for U.S. Appl. No. 13/463,803.

Supplementary European Search Report for EP20120779639, Virender K. Sharma, Nov. 13, 2014.

European Search Opinion for EP20120779639, Virender K. Sharma, Nov. 25, 2014.

(56) References Cited

OTHER PUBLICATIONS

Notice of Allowance dated Jan. 20, 2015 for U.S. Appl. No. 13/602,184.
Office Action dated Jun. 25, 2015 for U.S. Appl. No. 14/201,766.
Office Action dated Oct. 7, 2015 for U.S. Appl. No. 13/975,162.
Office Action for Chinese Patent Application No. 201280028867.7, May 4, 2015.
Second Office Action for Chinese Patent Application No. 201280028867.7, dated Mar. 21, 2016.
International Search Report for PCT/US2014/066578, Mar. 19, 2015.
Jameison, GG et al. "Laparoscopic Nissen Fundoplication". Annals of Surgery, vol. 220. No. 2, p. 139 (1994).
Tam, Wce et al. "Delivery of radiofrequency energy to the lower esophageal sphincter and gastric cardia inhibits transient oesophageal sphincter relaxations and gastro-oesophageal reflux in patients with reflux disease". Gut, 52 (4), 479-785 (2003).
International Search Report for PCT/US2014/066565, Mar. 12, 2015.
International Search Report for PCT/US2014/053793, Mar. 27, 2015.
Office Action dated Oct. 2, 2015 for U.S. Appl. No. 14/500,856.
Office Action dated Feb. 1, 2016 for U.S. Appl. No. 14/475,736.
Examination Report for New Zealand Patent Application No. 616944, Jun. 17, 2014.
Examination Report for New Zealand Patent Application No. 616944, Nov. 2, 2015.
Examination Report for Australian Patent Application No. 2012250686, Nov. 4, 2015.
Extended European Search Report for EPO Application No. 12771852.6, Aug. 28, 2014.
Examination Report for Australian Patent Application No. 2012242533, Oct. 5, 2015.
Notice of Allowance dated Jan. 20, 2016 for U.S. Appl. No. 14/201,766.
First Office Action for Chinese Patent Application No. 201380054290.1, Apr. 1, 2016.

* cited by examiner

IMPLANTABLE ELECTRICAL STIMULATION LEADS

CROSS-REFERENCE

The present application relies on U.S. Provisional Patent Application No. 61/769,732, entitled "Implantable Electrical Stimulation Leads" and filed on Feb. 26, 2013, for priority. The aforementioned application is herein incorporated by reference.

U.S. patent application Ser. No. 13/602,184, entitled "Endoscopic Lead Implantation Method", filed on Sep. 2, 2012, and assigned to the applicant of the present invention, is herein incorporated by reference in its entirety.

FIELD

The present specification relates generally to implantable leads used in the electrical stimulation of human tissues. More particularly, the present specification relates to implantable electrical stimulation leads useful in the stimulation of anatomical structures proximate the gastroesophageal junction.

BACKGROUND

Electrical stimulation of nerves and surrounding tissue is used to treat a variety of conditions. For example, electrical stimulation can be used to restore partial function to limbs or organs following traumatic injury. Electrical stimulation can also be used to reduce pain. Specifically, electrical stimulation can be used to treat disorders associated with the gastrointestinal (GI) system, such as, obesity and gastroesophageal reflux disease (GERD).

Obesity is a common condition and a major public health problem in developed nations including the United States of America. As of 2009, more than two thirds of American adults, approximately 127 million people, were either overweight or obese. Data suggest that 300,000 Americans die prematurely from obesity-related complications each year. Many children in the United States are also either overweight or obese. Hence, the overall number of overweight Americans is expected to rise in the future. It has been estimated that obesity costs the United States approximately $100 billion annually in direct and indirect health care expenses and in lost productivity. This trend is also apparent in many other developed countries.

For adults, the body mass index (BMI) is used to determine if one is overweight or obese. A person's BMI is calculated by multiplying body weight in pounds by 703 and then dividing the total by height in inches squared. A person's BMI is expressed as kilograms per meter squared. An adult is considered overweight if his or her BMI is between 25 and 30 kg/m2. Obesity is defined as possessing a BMI between 30 and 40 kg/m2. A BMI greater than 30 kg/m$^2$ is associated with significant co-morbidities. Morbid obesity is defined as possessing either a body weight more than 100 pounds greater than ideal or a body mass index (BMI) greater than 40 kg/m$^2$. Approximately 5% of the U.S. population meets at least one of the criteria for morbid obesity. Morbid obesity is associated with many diseases and disorders including, for example: diabetes; hypertension; heart attacks; strokes; dyslipidemia; sleep apnea; pickwickian syndrome; asthma; lower back and disc disease; weight-bearing osteoarthritis of the hips, knees, ankles and feet; thrombophlebitis and pulmonary emboli; intertriginous dermatitis; urinary stress incontinence; gastroesophageal reflux disease (GERD); gallstones; and, sclerosis and carcinoma of the liver. In women, infertility, cancer of the uterus, and cancer of the breast are also associated with morbid obesity. Taken together, the diseases associated with morbid obesity markedly reduce the odds of attaining an average lifespan. The sequelae raise annual mortality in affected people by a factor of 10 or more.

Gastro-esophageal reflux disease (GERD) is another common health problem and is expensive to manage in both primary and secondary care settings. This condition results from exposure of esophageal mucosa to gastric acid as the acid refluxes from the stomach into the esophagus. The acid damages the esophageal mucosa resulting in heartburn, ulcers, bleeding, and scarring, and long term complications such as Barrett's esophagus (pre-cancerous esophageal lining) and adeno-cancer of the esophagus.

Gastric electrical stimulation (GES) is aimed at treating both obesity and GERD. GES employs an implantable, pacemaker-like device to deliver low-level electrical stimulation to the gastrointestinal tract. For obesity, GES operates by disrupting the motility cycle and/or stimulating the enteric nervous system, thereby increasing the duration of satiety experienced by the patient. The procedure involves the surgeon suturing electrical leads to the outer lining of the stomach wall. The leads are then connected to the device, which is implanted just under the skin in the abdomen. Using an external programmer that communicates with the device, the surgeon establishes the level of electrical stimulation appropriate for the patient. The Abiliti® implantable gastric stimulation device, manufactured by IntraPace, is currently available in Europe for treatment of obesity.

In another example, Medtronic offers for sale and use the Enterra™ Therapy, which is indicated for the treatment of chronic nausea and vomiting associated with gastroparesis when conventional drug therapies are not effective. The Enterra™ Therapy uses mild electrical pulses to stimulate the stomach. According to Medtronic, this electrical stimulation helps control the symptoms associated with gastroparesis, including nausea and vomiting.

Electrical stimulation has also been suggested for use in the treatment of GERD, wherein the stimulation is supplied to the lower esophageal sphincter (LES). For example, in U.S. Pat. No. 6,901,295, assigned to Endostim, Inc., "A method and apparatus for electrical stimulation of the lower esophageal sphincter (LES) is provided. Electrode sets are placed in the esophagus in an arrangement that induce contractions of the LES by electrical stimulation of the surrounding tissue and nerves. The electrical stimulus is applied by a pulse generator for periods of varying duration and varying frequency so as to produce the desired contractions. The treatment may be short-term or may continue throughout the life of the patient in order to achieve the desired therapeutic effect. The stimulating electrode sets can be used either alone or in conjunction with electrodes that sense esophageal peristalsis. The electrode sets can be placed endoscopically, surgically or radiologically." The referenced invention relies on sensing certain physiological changes in the esophagus, such as changes in esophageal pH, to detect acid reflux. Once a change in esophageal pH is recognized, the system generates an electrical stimulation in an attempt to instantaneously close the LES and abort the episode of acid reflux. U.S. Pat. No. 6,901,295 is hereby incorporated by reference in its entirety.

The leads used in electrical stimulation of gastrointestinal tissues traditionally comprise elongated or coiled, insulated wires or cables having a means for attachment to an electrical pulse generator at one end and one or more exposed electrodes at the other end. The leads are typically anchored in place such that the electrodes are positioned and remain proximate the target nerve or tissues. Anchoring is often accomplished by suturing the electrode containing ends of the leads proximal to the electrodes and into the surrounding tissue. Traditional leads often comprise a needle attached to a length of suture nylon at the distal end of each branch of the lead. A butterfly shaped anchoring element is positioned on each branch just proximal to each electrode. The needle and suture nylon are used to create a pathway for the electrode to be inserted into the tissue, with the needle and most of the suture being removed thereafter. The remaining suture is used as a tether onto which at least one clip (e.g., titanium clip) is used to provide a distal stop thus preventing the electrode from backing out until sufficient fibrosis is formed.

While current electrical leads are effective in transmitting electrical stimulation to target nerves and tissues, they are not without their drawbacks. For example, the overall length of current leads limits the implantation site of the stimulator to which they connect. A lead that is intended to have its electrodes positioned proximate the gastroesophageal junction is often implanted through the abdominal wall via laparoscopy, but requiring the stimulator and its unsightly scar at the patient's exposed abdomen. Therefore, what is needed is a lead having an increased overall length to permit stimulator implantation at points further from the therapy site, whereby the scar could be covered by most clothing apparel (e.g., male and female swimsuits) or the implant access could be through the umbilicus.

In addition, with regard to bipolar leads, the monopolar branches that extend beyond the bifurcation point are often too long. Lengthy monopolar branches can become entangled in surrounding tissues, leading to dislodgment of anchored leads and stricture formation. Therefore, what is needed is a bipolar lead having shortened monopolar branches. Further, traditional leads are often pulled backward to facilitate anchoring, causing the proximal 2 to 3 mm of conductive material to become exposed. Exposed conductive material can result in inadvertent electrical stimulation of non-target tissues as well as less stimulation current reaching the target tissues. Therefore, what is also needed is a lead having additional insulation closer to the electrodes.

Traditional leads also include electrodes that are too large for certain applications, including stimulation of the gastroesophageal junction. Oversized electrodes can also result in inadvertent electrical stimulation of non-target tissues. Therefore, what is needed is a lead having smaller sized electrodes. In addition, the space in which to work surrounding the gastroesophageal junction (GEJ) is relatively confined compared to other spaces, such as, around the body of the stomach. Traditional leads having long suture nylons tempt the surgeon to use the same needle and suture for anchoring the lead proximal to the electrode; however, this suture material is chosen for applying distal clips and not anchoring the leads. Therefore, what is also needed is a lead having shorter suture nylons on each branch such that this needle and suture is not long enough to be used for anchoring the leads proximal to the electrode. Having shorter suture nylons also reduces the number of pulling maneuvers required in order to bring the electrode(s) into final position. Traditional leads often include a curved needle for anchoring. The degree of curvature of the needle is often not sufficient when considering the adjacent tissues, resulting in injury to the tissue. What is needed is a needle curvature which will allow the user to significantly bury the electrode within the target tissue while also making the needle easily retrievable from the tissue exit site without puncturing or scraping nearby tissues.

Therefore, what is needed specifically for GEJ implantation is a lead having a needle with a degree of curvature specific to the target and surrounding tissue. Some traditional leads include an additional suture sleeve over the lead body to prevent damage to surrounding tissues during implantation. However, this sleeve tends to attract much fibrosis. Therefore, what is also needed is a lead having no additional anchoring sleeve.

Traditional leads are often implanted laparoscopically via an incision site on the abdomen. The incision typically leaves several visible scars and use of anchoring needles usually results in some trauma to the internal tissues. Applying suture anchors through an endoscope are difficult, specifically in the confined space of the GEJ or in a small endoscopic tunnel. Therefore, there is also a need for an electrical lead that can be implanted using an endoscope and can be anchored to surrounding tissues without using needles and sutures.

SUMMARY

The present specification discloses an implantable electrical lead for use in the stimulation of biological tissues, said lead comprising: an elongate lead body having a proximal end and a distal end, said lead body comprising an electrically conductive inner coil, an electrically conductive outer coil, a first insulating sheath covering said inner coil, and a second insulating sheath covering said outer coil wherein said lead body has a length within a range of 390 mm to 490 mm; a connector attached to and in electrical communication with said proximal end of said lead body; a first elongate branch having a proximal end and a distal end, said first elongate branch comprising said inner coil and said first insulating sheath covering said inner coil and not comprising said outer coil and said second insulating sheath, wherein said first branch has a length within a range of 50 mm to 120 mm; a second elongate branch having a proximal end and a distal end, said second elongate branch comprising said outer coil and said second insulating sheath covering said outer coil and not comprising said inner coil and said first insulating sheath, wherein said proximal end of said first branch and said proximal end of said second branch join to form said distal end of said lead body, wherein said second branch has a length within a range of 50 mm to 120 mm; a first anchoring element and a first electrode attached to said first branch and positioned proximate said distal end of said first branch; and, a second anchoring element and a second electrode attached to said second branch and positioned proximate said distal end of said second branch.

Optionally, in one embodiment, the implantable electrical lead further comprises a first length of suturing material and a second length of suturing material, each having a proximal end and a distal end, wherein said proximal end of said first length of said suturing material is attached to said distal end of said first branch and said proximal end of said second length of said suturing material is attached to said distal end of said second branch. In various embodiments, the first and second lengths of suturing material are each in a range of 55 to 65 mm. In one embodiment, the implantable electrical lead further comprises a first needle attached to said distal end of said first length of suturing material and a second needle attached to said distal end of said second length of suturing material, wherein said first needle and said first length of suturing material are used to suture said first anchoring element to a biological tissue and said second needle and said second length of suturing material are used to suture said second anchoring element to a biological tissue. In various embodiments, the first and second needles are each within a range of ¼ to ⅜ of a circle curve needles with a length ranging from 18 to 23 mm and include a base having a diameter in a range of 0.68 mm to 0.78 mm.

Optionally, in one embodiment, wherein a distal end of said outer coil is positioned at said distal end of said lead body, said lead further comprises an additional electrically conductive coil having a proximal end and a distal end and comprising said second branch, wherein said proximal end of said additional coil is attached to said distal end of said outer coil and said second anchoring element and said second electrode are attached to and positioned proximate said distal end of said additional coil and said second insulating sheath extends over said additional coil.

Optionally, in one embodiment, the implantable electrical lead further comprises a sleeve covering the distal end of said lead body and the proximal ends of said first branch and said second branch.

Optionally, in one embodiment, the implantable electrical lead further comprises a marking element on said first branch to serve as a visual indicator.

Optionally, in one embodiment, said first insulating sheath extends over a proximal portion of said first electrode and said second insulating sheath extends over a proximal portion of said second electrode such that, after said lead is implanted, said insulating sheaths are pulled partially in a proximal direction to expose said proximal portions of said electrodes. In various embodiments, the first and second insulating sheaths extend in a range of 1 to 5 mm over said first and second electrodes. In various embodiments, after said lead is implanted, a total exposed length of said electrodes is in a range of 1 to 10 mm.

The present specification also discloses a lead delivery catheter to be used with an endoscope or a laparoscope and for implanting the electrical stimulation lead described above in the body of a patient, said catheter comprising: a catheter body having a proximal end, a distal end, and a lumen within; an inflatable balloon attached to said distal end of said catheter body; and, a grasping mechanism attached to said distal end of said catheter body for grasping said lead.

Optionally, in one embodiment, the catheter further comprises a light source providing illumination at its distal end.

Optionally, in one embodiment, the catheter further comprises a camera at its distal end.

Optionally, in one embodiment, the catheter further comprises a bipolar electrocautery electrode at its distal end. In one embodiment, the bipolar electrocautery electrode is incorporated into said grasping mechanism.

The present specification also discloses an implantable electrical lead for use in the stimulation of biological tissues, said lead comprising: a Y shaped structure comprising a central portion, having a proximal end and a distal end, a first prong, and a second prong, each prong having a proximal end and a distal end, wherein said proximal ends of said first and second prongs join together to form said distal end of said central portion, further wherein: said central portion comprises an electrically conductive inner coil covered by a first insulating sheath and an electrically conductive outer coil covered by a second insulating sheath, wherein said outer coil covered by said second insulating sheath is positioned coaxially over said inner coil covered by said first insulating sheath and said central portion has a length within a range of 390 mm to 490 mm, further wherein a connector is attached to and in electrical communication with said proximal end of said central portion; said first prong comprises said inner coil covered by said first insulating sheath and does not comprise said outer coil covered by said second insulating sheath, wherein said first prong has a length within a range of 50 mm to 120 mm, further wherein a first anchoring element and a first electrode are attached to said first prong and are positioned proximate said distal end of said first prong, said first anchoring element configured to permit the ingrowth of biological tissues; said second prong comprises said outer coil covered by said second insulating sheath and does not comprises said inner coil covered by said first insulating sheath, wherein said second prong has a length within a range of 50 mm to 120 mm, further wherein a second anchoring element and a second electrode are attached to said second prong and positioned proximate said distal end of said second prong, said second anchoring element configured to permit the ingrowth of biological tissues; and, a length of suturing material having a first end and a second end, wherein said first end of said length of suturing material is attached to said distal end of said first prong and said second end of said length of suturing material is attached to said distal end of said second prong, joining said first and second prongs, said length of suturing material forming a loop.

In various embodiments, the length of suturing material is in a range of 10 to 150 mm.

Optionally, in one embodiment, wherein a distal end of said outer coil is positioned at said distal end of said central portion, said lead further comprises an additional electrically conductive coil having a proximal end and a distal end and comprising said second prong, wherein said proximal end of said additional coil is attached to said distal end of said outer coil and said distal end of said additional coil is attached to said second end of said length of suturing material, further wherein said second anchoring element and said second electrode are attached to and positioned proximate said distal end of said additional coil and said second insulating sheath extends over said additional coil.

The present specification also discloses a method of implanting an electrical stimulation lead having a connector, a first branch with a first electrode and first anchoring element and a second branch with a second electrode and second anchoring element, into a patient, said method comprising the steps of: inserting a distal end of an endoscope into a natural orifice of said patient; inserting a lead delivery catheter into a working channel of said endoscope, said lead delivery catheter comprising: a catheter body having a proximal end, a distal end, and a lumen within; an inflatable balloon attached to said distal end of said catheter body; and, a grasping mechanism attached to said distal end of said catheter body for grasping said lead; creating an incision in the internal wall of a body cavity entered via said orifice; advancing said distal end of said catheter through said incision into a target anatomy area, wherein said target anatomy area comprises the outer walls of the esophagus and stomach and surrounding tissues proximate the gastroesophageal junction (GEJ); inserting a laparoscope having a proximal end, a distal end, and a lumen within into an abdomen of said patient such that said distal end is positioned proximate said target anatomy area; placing said lead within said lumen of said laparoscope through said proximal end of said laparoscope; pulling on said loop of said lead via said grasping mechanism on said catheter to draw said lead into said target anatomy area; positioning the first branch and the second branch of said lead such that said first and second electrodes are positioned proximate the target anatomy; positioning said first anchoring element and said second anchoring element proximate surrounding tissues to permit growth of said surrounding tissues into said anchoring elements to secure said branches; and, attaching said connector of said lead to an electrical pulse generator.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings.

DETAILED DESCRIPTION

Figure 1A:
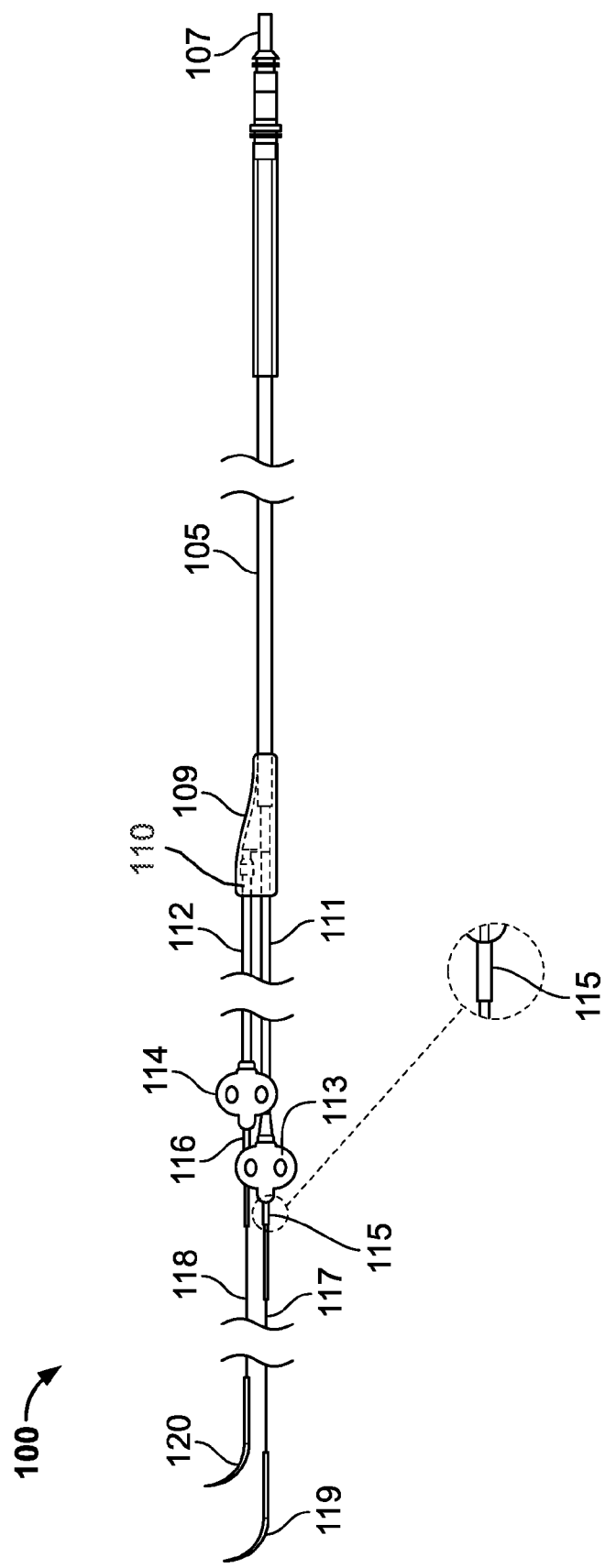
FIG. 1A is a side view illustration of one embodiment of an implantable electrical stimulation lead of the present specification.

The present specification discloses an implantable electrical stimulation lead that is dimensioned specifically for use in confined anatomy, particularly the area proximate the gastroesophageal junction (GEJ). The lead is designed to be implanted laparoscopically and includes needles for suturing anchoring elements to the neighboring anatomy. The present specification also discloses another, needleless implantable electrical stimulation lead that is designed to be implanted through the working channel of an endoscope and includes anchoring elements that eliminate the need for suturing the lead to surrounding tissues. The present specification also discloses a lead delivery catheter used for implanting the needleless electrical stimulation lead through the working channel of an endoscope. The present invention is directed toward multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

In one embodiment, an implantable electrical stimulation lead is a bipolar lead and comprises an elongate lead body having a proximal end and a distal end. The lead body is comprised of an electrically conductive material with an overlaying insulating sheath. Attached to the proximal end is a coupling means for connecting the lead to a pulse generator such that the two are in electrical communication. In one embodiment, the coupling means is an international standard (IS-1) connector system. The distal end of the lead body includes a bifurcation sleeve. In one embodiment, the electrically conductive material of the lead body includes an inner coil and an outer coil, electrically insulated from each other, which split into separate branches within the bifurcation sleeve.

The inner coil and outer coil continue distally beyond the bifurcation sleeve as first and second monopolar branches. In one embodiment, the first and second monopolar branches comprise first and second elongate branch bodies respectively, each having a proximal end and a distal end. In one embodiment, the first branch body of the first monopolar branch comprises the continuation of the inner coil of the lead body and the second branch body of the second monopolar branch comprises a partial continuation of the outer coil of lead body attached to an additional coil. The additional coil is an elongate coil having a proximal end and a distal end with its proximal end attached to the distal end of the outer coil. In another embodiment, the first branch body of the first monopolar branch comprises the continuation of the inner coil of the lead body and the second branch body of the second monopolar branch comprises the continuation of the outer coil of lead body. The proximal ends of the first and second branch bodies join together within the bifurcation sleeve as described above. The distal ends of the first and second branch bodies each have a length of suturing material attached to them. In one embodiment, the suture is a monofilament using nylon as the material. Attached to the distal end of each length of suturing material is a needle. In one embodiment, the needle is a curved needle. In one embodiment, the needle is a straight needle. Both the first and second branch bodies additionally include at least one anchor and at least one electrode. Each electrode is in electrical communication with either the inner or outer coil of its respective branch body. In one embodiment, the anchor has a butterfly shape with two holes, one on each side, for passing the needle and suture material during anchoring. Each electrode is positioned just distal to each anchor. In one embodiment, the first monopolar branch has a length that is longer than that of the second monopolar branch. In another embodiment, the first and second monopolar branches have the same length.

In one embodiment, a portion of each electrode is insulated by a length of tubing. In one embodiment, the tubing extends distally from the distal end of the anchoring element. In one embodiment, the tubing and anchoring element are composed of silicone.

The lead is designed to be implanted using a standard laparoscopic technique common in the prior art.

In another embodiment, an implantable electrical stimulation lead is intended for implantation via the working channel of an endoscope and includes anchoring elements rather than a needle and sutures for anchoring. In this embodiment, the implantable electrical stimulation lead is a bipolar lead and also comprises an elongate lead body having a proximal end and a distal end. The lead body is comprised of an electrically conductive material with an overlaying insulating sheath. Attached to the proximal end is a coupling means for connecting the lead to a pulse generator such that the two are in electrical communication. In one embodiment, the coupling means is an IS-1 connector system. The distal end of the lead body includes a bifurcation sleeve. In one embodiment, the electrically conductive material of the lead body includes an inner coil and an outer coil, electrically insulated from each other, which split into separate branches within the bifurcation sleeve.

The inner coil and outer coil continue distally beyond the bifurcation sleeve as first and second monopolar branches. In one embodiment, the first and second monopolar branches comprise first and second elongate branch bodies respectively, each having a proximal end and a distal end. In one embodiment, the first branch body of the first monopolar branch comprises the continuation of the inner coil of the lead body and the second branch body of the second monopolar branch comprises a partial continuation of the outer coil of lead body attached to an additional coil. The additional coil is an elongate coil having a proximal end and a distal end with its proximal end attached to the distal end of the outer coil. In another embodiment, the first branch body of the first monopolar branch comprises the continuation of the inner coil of the lead body and the second branch body of the second monopolar branch comprises the continuation of the outer coil of lead body. The proximal ends of the first and second branch bodies join together within the bifurcation sleeve as described above. The distal ends of the first and second branch bodies are connected by a suture loop. The suture loop is designed to be grasped with endoscopic graspers and pulled through the working channel of the endoscope. In one embodiment, the material of the suture loop is silk. Both the first and second branch bodies additionally include at least one anchoring element and at least one electrode. Each electrode is in electrical communication with either the inner or outer coil of its respective branch body. The anchoring elements allow for fibrosis around them in the created endoscopic tunnel so that the electrodes remain in position. This eliminates the need for suturing the lead branches in place. In various embodiments, the anchoring element is a silicone sleeve having grooves, spikes, or holes to allow for the ingrowth of fibrous tissue and anchoring. In another embodiment, the anchoring element is comprised of a porous material that allows fibrous ingrowth and anchoring. In one embodiment, the porous material is a Dacron mesh. In another embodiment, the anchoring material is made of an electrically conductive material, such as platinum-iridium alloy, and is electrically connected to the electrode to increase the area of stimulation. In another embodiment, the electrodes are the anchors, with special shapes, such as barbs, to facilitate anchoring and tissue in-growth. Each electrode is positioned just distal to each anchor. In one embodiment, the first monopolar branch has a length that is longer than that of the second monopolar branch such that the electrodes are staggered in an in-line position. In another embodiment, the first and second monopolar branches have the same length.

The present specification also discloses a lead delivery catheter for use during the implantation of the needleless electrical stimulation lead through the working channel of an endoscope. In one embodiment, the catheter is used with the natural orifice transluminal endoscopic surgery (NOTES) technique to implant one or more leads proximate the lower esophageal sphincter (LES) using an endoscopic approach or a laparoscopic approach. In one embodiment, the catheter includes a catheter body having a proximal end, a distal end, and a lumen within. The catheter includes an inflatable balloon, a grasping mechanism, and a light source at its distal end. Optionally, in one embodiment, the catheter includes a camera at its distal end. Optionally, in one embodiment, the catheter includes a bipolar electrode at its distal end for electrocautery.

The leads disclosed in the various embodiments of the present specification can be implanted into a patient using the methods described in U.S. patent application Ser. No. 13/602,184, entitled "Endoscopic Lead Implantation Method", filed on Sep. 2, 2012, and assigned to the applicant of the present invention, which is herein incorporated by reference in its entirety.

Figure 1B:
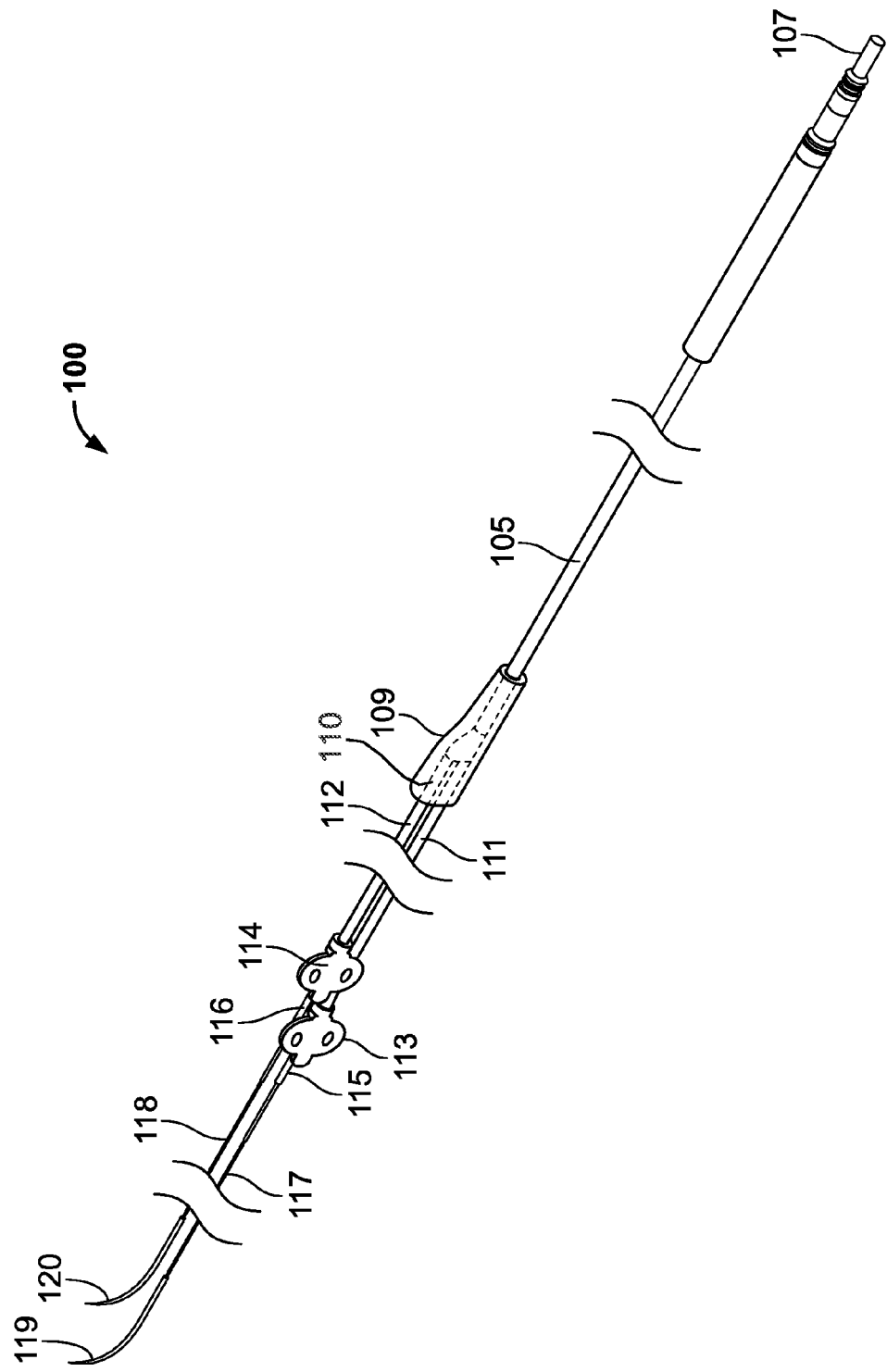
FIG. 1B is an oblique side view illustration of the embodiment of the implantable electrical stimulation lead of FIG. 1A.

FIGS. 1A and 1B are side and oblique side view illustrations respectively, of one embodiment of an implantable electrical stimulation lead 100 of the present specification. The lead 100 is a bipolar lead and includes an elongate lead body 105 having a proximal end and a distal end. The lead body 105 is comprised of an electrically conductive inner coil and an electrically conductive outer coil. The inner coil and outer coil are each covered by an insulating sheath. An IS-1 connector system 107, having proximal and distal ends, is attached to the proximal end of the lead body 105 and a bifurcation sleeve 109, having proximal and distal ends, is coupled to the distal end of the lead body 105. In various embodiments, the length of the lead body 105, from the proximal end of the IS-1 connector pin 107 to the distal end of the bifurcation sleeve 109, is in a range of 390 mm to 490 mm. In one embodiment, the length of the lead body 105, from the proximal end of the IS-1 connector pin 107 to the distal end of the bifurcation sleeve 109, is 433 mm. This length is greater than that encountered in the prior art, which often measures approximately 350 mm. The greater length allows for greater variation in implantation site. A physician can implant the lead from a more cosmetically pleasing position, for example, a sub-bikini line implantation site or a transumbilical implantation site. The resulting stimulator implant scar would not be visible on the patient's abdomen. In addition, the greater length allows for appropriate routing of the lead to prevent entanglement in the small bowel or a gravid uterus in a female with child bearing potential.

The inner and outer coils of the lead body 105 separate within the bifurcation sleeve 109 and continue distally as monopolar branches. Referring to FIGS. 1A and 1B, the inner coil continues distally from the distal end of the bifurcation sleeve 109 as a first monopolar branch 111, having proximal and distal ends, and the outer coil continues distally from the distal end of the bifurcation sleeve 109 and attaches to an additional coil 110 having proximal and distal ends, which continues as a second monopolar branch 112 having proximal and distal ends. In another embodiment, the outer coil continues distally from the distal end of the bifurcation sleeve 109 as the second monopolar branch 112 having proximal and distal ends. The first monopolar branch 111 comprises the inner coil with a covering insulating sheath and includes an anchor 113, having a proximal end and a distal end, and an insulated electrode 115, having a proximal end and a distal end, at a point proximate its distal end. The electrode 115 is positioned just distal to the anchor 113. Attached to the distal end of the first monopolar branch 111 is a length of suture material 117, itself having a proximal end and a distal end. In one embodiment, the suture material is composed of nylon. Attached to the distal end of the suture material is a suture needle 119. The second monopolar branch 112 comprises a portion of the outer coil and an attached additional coil 110 with a covering insulating sheath and includes an anchor 114, having a proximal end and a distal end, and an insulated electrode 116, having a proximal end and a distal end, at a point proximate its distal end. The electrode 116 is positioned just distal to the anchor 114. Attached to the distal end of the second monopolar branch 112 is a length of suture material 118, itself having a proximal end and a distal end. In one embodiment, the suture material is composed of nylon. Attached to the distal end of the suture material is a suture needle 120.

In another embodiment, each branch includes an additional suture with needle and the anchor, in a butterfly shape, is positioned just distal to the bifurcation sleeve. The additional suture and position of the anchor will help maintain the anchor flat on the esophagus after implantation. This will prevent the anchor from pivoting and avoid extra pressure on the esophageal wall.

FIG. 1A also includes a close-up view illustration of the insulated electrode 115 of the first monopolar branch 111. In one embodiment, the electrode 115 includes a covering length of insulating material which will be discussed further with reference to FIG. 3 below. In another embodiment, the electrode is not covered by any insulating material.

Figure 2:
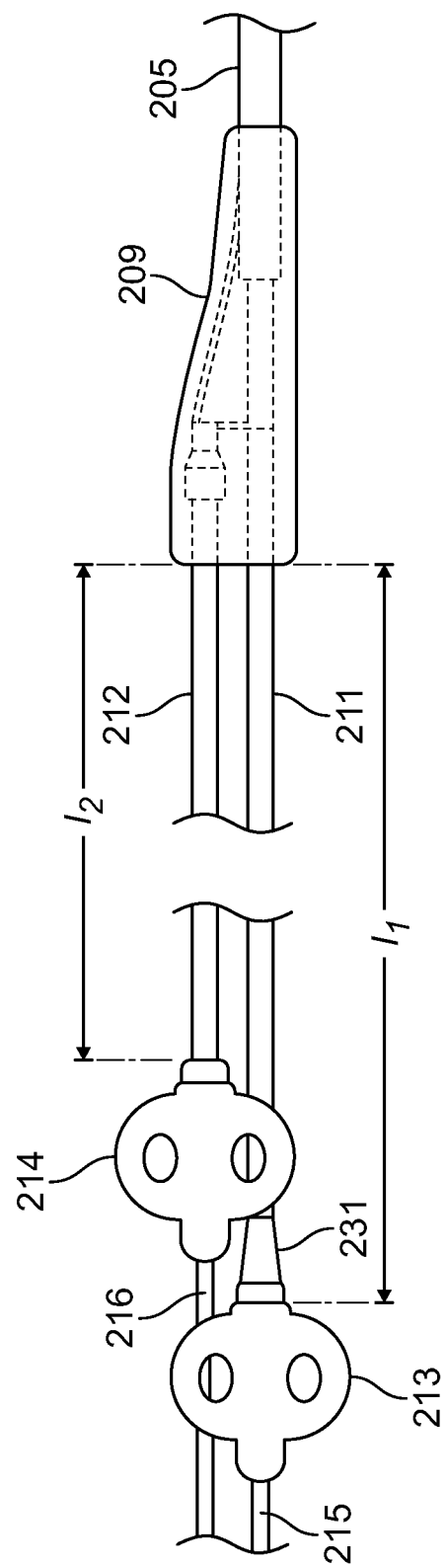
FIG. 2 is a close-up view illustration of the first and second monopolar branches of the embodiment of the implantable electrical stimulation lead of FIG. 1A.

FIG. 2 is a close-up view illustration of the first 211 and second 212 monopolar branches of the embodiment of the implantable electrical stimulation lead of FIG. 1A. The monopolar branches 211, 212 are depicted emanating distally from the distal end of the bifurcation sleeve 209. Also depicted is the distal end of the lead body 205 coupled to the bifurcation sleeve 209. The first monopolar branch 211 includes an anchor 213 and an insulated electrode 215 at a point proximate its distal end and the second monopolar branch 212 includes an anchor 214 and an insulated electrode 216 at a point proximate its distal end. In various embodiments, the length $l_1$ of the first monopolar branch 211, from its proximal end where it exits the distal end of the bifurcation sleeve 209 to its distal end where it meets the proximal end of the anchor 213, is in a range of 50 mm to 120 mm. In one embodiment, the length $l_1$ of the first monopolar branch 211, from its proximal end where it exits the distal end of the bifurcation sleeve 209 to its distal end where it meets the proximal end of the anchor 213, is 70 mm. This is shorter than the length encountered in the prior art, which is approximately 90 mm. In various embodiments, the length $l_2$ of the second monopolar branch 212, from its proximal end where it exits the distal end of the bifurcation sleeve 209 to its distal end where it meets the proximal end of the anchor 214, is in a range of 50 mm to 120 mm. In one embodiment, the length $l_2$ of the second monopolar branch 212, from its proximal end where it exits the distal end of the bifurcation sleeve 209 to its distal end where it meets the proximal end of the anchor 214, is 60 mm. This is shorter than the length encountered in the prior art, which is approximately 90 mm.

The longer length of the monopolar branches in the prior art facilitates their implantation across the gastric greater curvature, with one electrode on each wall. The shorter lengths of the monopolar branches of the lead of the current embodiment facilitate placement about the GEJ, where the anatomy in more confined. In one embodiment, the first monopolar branch 211 further includes a visual indicator 231 at its distal end, just proximal to the anchor 213. The visual indicator 231 indicates to the physician that this lead contains the inner coil of the lead body. In one embodiment, the visual indicator 231 is a black marking on the insulation of the first monopolar branch 211. Having monopolar branches of different lengths allows the physician to implant the electrodes in-line with each other.

Figure 3:
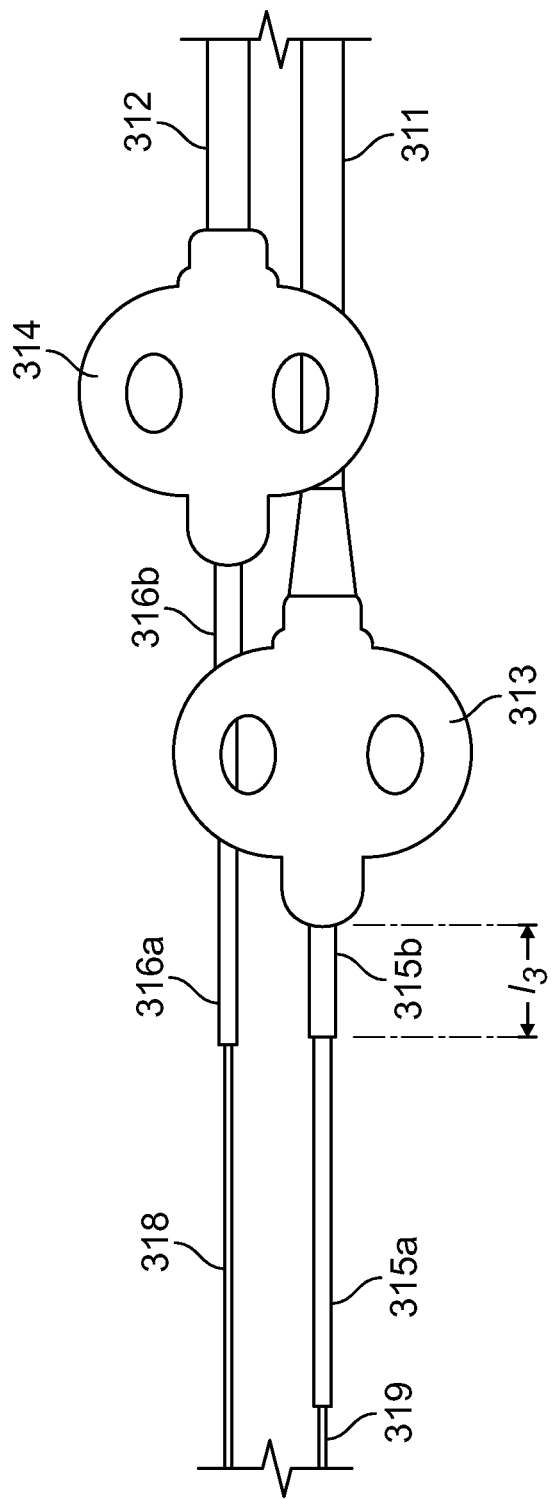
FIG. 3 is a close-up view illustration of the anchors and insulated proximal portions of the electrodes of the monopolar branches of the embodiment of the implantable electrical stimulation lead of FIG. 1A.

FIG. 3 is a close-up view illustration of the anchors 313, 314 and insulated proximal portions of the electrodes 315b, 316b of the monopolar branches 311, 312 of the embodiment of the implantable electrical stimulation lead of FIG. 1A. In one embodiment, the electrode of the first monopolar branch 311 comprises an exposed portion 315a and an insulated, unexposed portion 315b that is covered by a length of insulating tubing. In various embodiments, the length $l_3$ of the insulating tubing covering the insulated portion of the electrode 315b is in a range of 1 mm to 5 mm. In one embodiment, the length $l_3$ of the insulating tubing covering the insulated portion of the electrode 315b is 3 mm. In one embodiment, the insulating tubing is attached to the distal end of the anchor 313. Depicted attached to the distal end of the exposed portion of the electrode 315a is the proximal end of a length of suture material 319. In another embodiment, the electrode of the first monopolar branch does not include any insulating tubing and is exposed along its entire length (not shown).

In one embodiment, the electrode of the second monopolar branch 312 comprises an exposed portion 316a and an insulated, unexposed portion 316b that is covered by a length of insulating tubing. In various embodiments, the length of the insulating tubing covering the insulated portion of the electrode 316b of the second monopolar branch 312 is the same as the length of the insulating tubing covering the insulated portion of the electrode 315b of the lead of the first monopolar branch 311, that is, in a range of 1 mm to 5 mm. In one embodiment, the length of the insulating tubing covering the insulated portion of the electrode 316b of the second monopolar branch 312 is the same as the length of the insulating tubing covering the insulated portion of the electrode 315b of the lead of the first monopolar branch 311, that is, 3 mm. In one embodiment, the insulating tubing covering the insulated portion of the electrode 316b is attached to the distal end of the anchor 314. Depicted attached to the distal end of the exposed portion of the electrode 316a is the proximal end of a length of suture material 318. In another embodiment, the electrode of the second monopolar branch does not include any insulating tubing and is exposed along its entire length (not shown).

The insulating tubing covering the insulated, unexposed portions of the electrodes 315b, 316b serve to prevent the exposure of the proximal 2 to 3 mm of each electrode that often occurs during anchoring as the electrodes are pulled backward slightly over time.

In one embodiment, the insulating tubing covering the insulated portions of the electrodes 315b, 316b is composed of silicone. In various embodiments, the wall thickness of the insulating tubing is in a range of 0.160 mm to 0.170 mm. In one embodiment, the wall thickness of the insulating tubing is 0.165 mm (0.0065 in). In one embodiment, the anchors 313, 314 are composed of silicone. In one embodiment, the electrodes are composed of platinum-iridium (Pt—Ir). In various embodiments, the exposed portion of the electrodes 315a, 316a, after anchoring, is in a range of 1 mm to 10 mm. In one embodiment, the exposed portion of the electrodes 315a, 316a, after anchoring, is 5 mm. This length is shorter than the average of approximately 10 mm encountered in the prior art. The shorter electrodes have a higher charge density which has been shown to contribute to better results.

Figure 4:
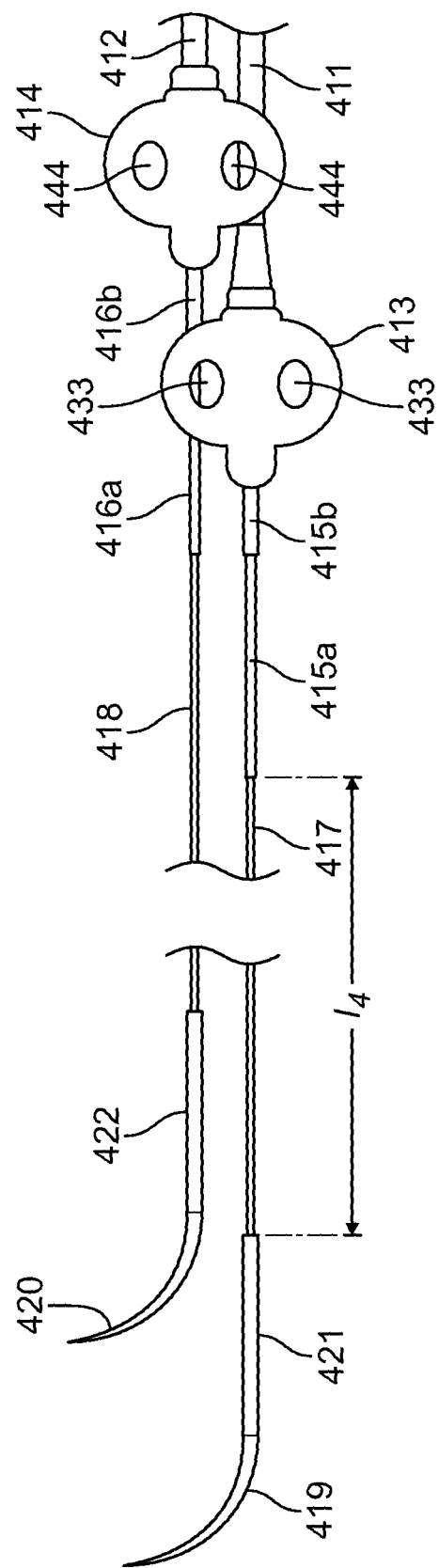
FIG. 4 is a close-up view illustration of the lengths of suture material attached to the distal ends of the monopolar branches of the embodiment of the implantable electrical stimulation lead of FIG. 1A.

FIG. 4 is a close-up view illustration of the lengths of suture material 417, 418 attached to the distal ends of the monopolar branches 411, 412 of the embodiment of the implantable electrical stimulation lead of FIG. 1A. Also depicted are the anchors 413, 414, exposed electrode portions 415a, 415b, and insulating tubing covering the insulated portions of the electrodes 415b, 416b of the first 411 and second 412 monopolar branches. Attached to the distal end of the first monopolar branch 411 and extending distally from the exposed portion of electrode 415a is a first length of suture material 417. The length of suture material 417 includes a proximal end and a distal end. A suture needle 419 is attached to the distal end of the suture material 417 via a coupling means 421. In various embodiments, the length $l_4$ of the suture material 417 is in a range of 55 mm to 65 mm. In one embodiment, the length $l_4$ of the suture material 417 is 60 mm.

Attached to the distal end of the second monopolar branch 412 and extending distally from the exposed portion of electrode 416a is a second length of suture material 418. The length of suture material 418 includes a proximal end and a distal end. A suture needle 420 is attached to the distal end of the suture material 418 via a coupling means 422. In various embodiments, the length of the suture material 418 attached to the distal end of the second monopolar branch 412 is the same as the length of the suture material 417 attached to the distal end of the first monopolar branch 411, that is, in a range of 55 mm to 65 mm. In one embodiment, the length of the suture material 418 attached to the distal end of the second monopolar branch 412 is the same as the length of the suture material 417 attached to the distal end of the first monopolar branch 411, that is, 60 mm.

The average length of the suture material encountered in leads in the prior art is approximately 112 mm. For applications at the GEJ, such a length requires the physician to perform additional, unnecessary pulling maneuvers in order to properly position the anchors. The area to maneuver proximate the GEJ is limited by the proximity of the GEJ to the diaphragm. Therefore, a lead with shorter lengths of suture material is advantageous for such an application.

In one embodiment, the suture material is composed of nylon. In another embodiment, the suture material is barbed, such as V-Loc™ by Covidien, to improve anchoring of the electrodes. During anchoring, a physician sutures the branches into position by threading the needles 419, 420 through holes 433, 444 in the anchors 413, 414 and into the surrounding tissue. In one embodiment, the anchors 413, 414 have a butterfly shape with two holes 433, 444 positioned on either side of each monopolar branch 411, 412.

Figure 5:
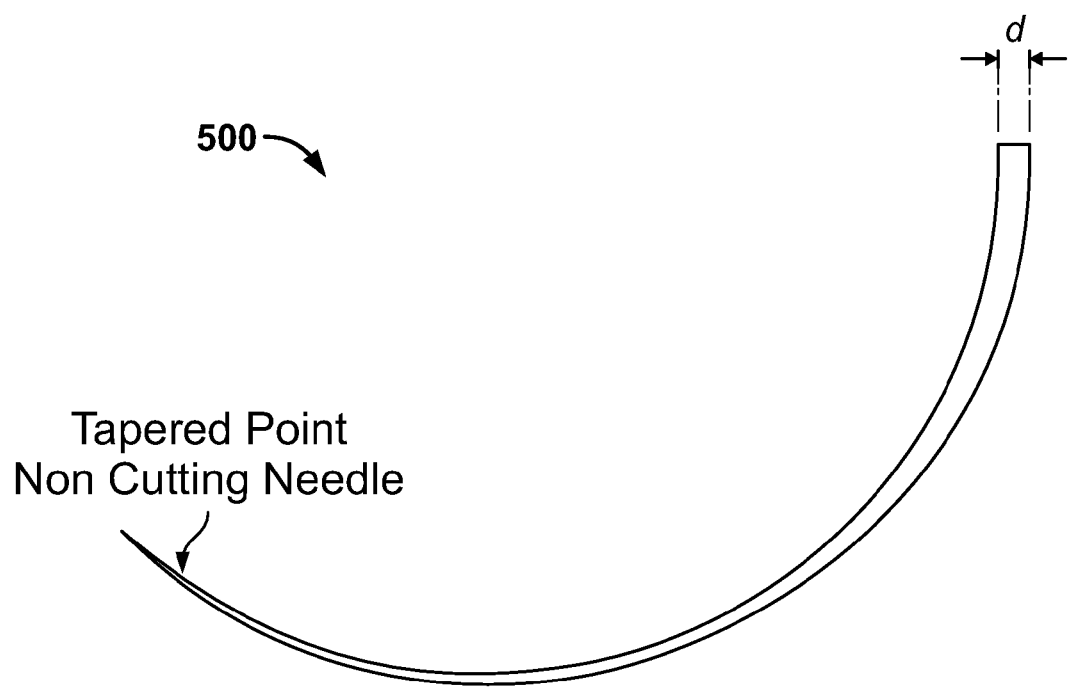
FIG. 5 is a close-up view illustration of the needle used to suture in place the anchors of the embodiment of the implantable electrical stimulation lead of FIG. 1A.

FIG. 5 is a close-up view illustration of the needle 500 used to suture in place the anchors of the embodiment of the implantable electrical stimulation lead of FIG. 1A. A needle 500 is attached to the distal end of each length of suture material emanating from the distal end of each monopolar branch. In one embodiment, each needle 500 is attached to the distal end of the suture material via a coupling means. In one embodiment, each needle 500 is a ⅜ of a circle curve needle and has a length within a range of 18 to 23 mm. In another embodiment, each needle 500 is a ¼ of a circle curve needle and has a length within a range of 18 to 23 mm. The needle 500 has a tapered point and is a non-cutting needle. In various embodiments, the needle has a diameter d at its base in a range of 0.68 mm to 0.78 mm, being at least as large as the diameter of the insulated or non-insulated electrode. In one embodiment, the needle has a diameter d at its base of 0.73 mm (0.029 in), which is 0.56 mm (0.022 in) larger than the insulating tubing of the electrode.

During anchoring, the electrode tract should be straight. Traditional ½ curve sky shaped or ski needles encountered in the prior art start with a tight bend and hence require a circular maneuver. With such a needle, when a straight bite is attempted, the tissue is often heavily injured, similar to what occurs with a biopsy. The needle of the present embodiment, having a shorter curve, can be more easily straightened when maneuvering near the GEJ when compared to the needles of the prior art. In addition, suturing needles and leads encountered in the prior art often include a suture sleeve. Such sleeves tend to attract fibrosis. The lead of the present specification does not include a sleeve so as to minimize fibrosis.

Figure 6:
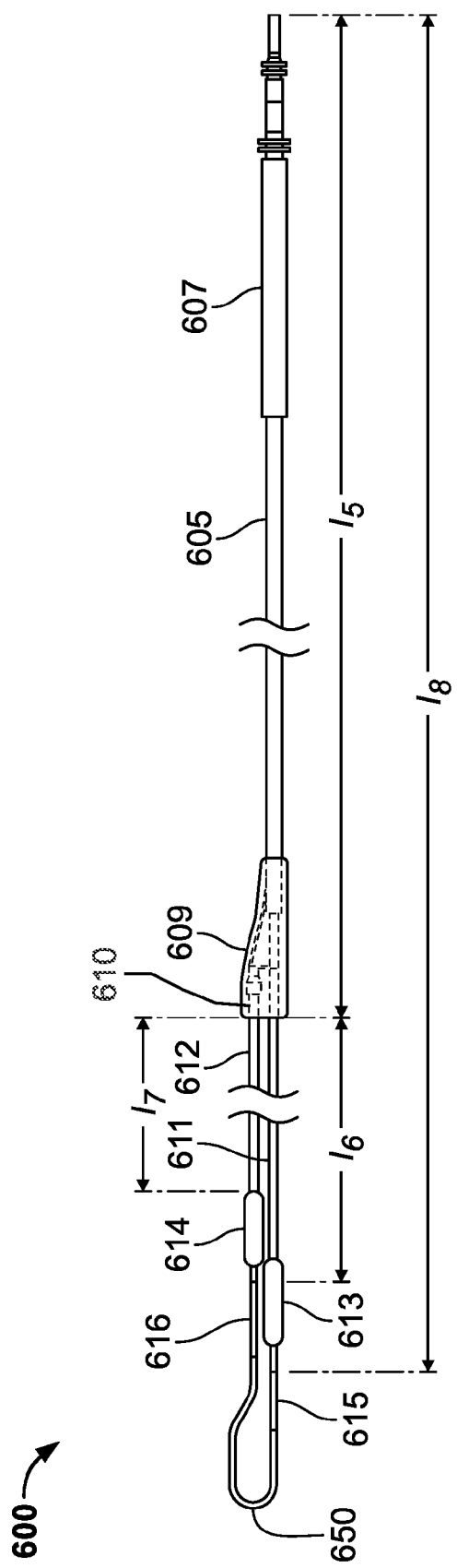
FIG. 6 is a side view illustration of another embodiment of an implantable electrical stimulation lead, depicting a length of suture material joining the distal ends of the two monopolar branches.

FIG. 6 is a side view illustration of another embodiment of an implantable electrical stimulation lead 600, depicting a length of suture material 650 joining the distal ends of the two monopolar branches 611, 612. The lead 600 is a bipolar lead and includes an elongate lead body 605 having a proximal end and a distal end. The lead body 605 is comprised of an electrically conductive inner coil and an electrically conductive outer coil. The outer coil is covered by an insulating sheath. An IS-1 connector system 607, having proximal and distal ends, is attached to the proximal end of the lead body 605 and a bifurcation sleeve 609, having proximal and distal ends, is coupled to the distal end of the lead body 605. In various embodiments, the length $l_5$ of the lead body 605, from the proximal end of the IS-1 connector system 607 to the distal end of the bifurcation sleeve 609, is in a range of 390 mm to 490 mm. In one embodiment, the length $l_5$ of the lead body 605, from the proximal end of the IS-1 connector system 607 to the distal end of the bifurcation sleeve 609, is 433 mm.

The inner and outer coils of the lead body 605 separate within the bifurcation sleeve 609 and continue distally as monopolar branches. The inner coil continues distally from the distal end of the bifurcation sleeve 609 as a first monopolar branch 611, having proximal and distal ends, and a portion of the outer coil continues distally from the distal end of the bifurcation sleeve 609 and attaches to an additional coil 610, having proximal and distal ends, which continues as a second monopolar branch 612 having proximal and distal ends. In another embodiment, the outer coil continues distally from the distal end of the bifurcation sleeve 609 as the second monopolar branch 612 having proximal and distal ends. The first monopolar branch 611 comprises the inner coil with a covering insulating sheath and includes an anchor 613, having a proximal end and a distal end, and an electrode 615, having a proximal end and a distal end, at a point proximate its distal end. The electrode 615 is positioned just distal to the anchor 613. The second monopolar branch 612 comprises a portion of the outer coil and an attached additional coil 610 with a covering insulating sheath and includes an anchor 614, having a proximal end and a distal end, and an electrode 616, having a proximal end and a distal end, at a point proximate its distal end. The electrode 616 is positioned just distal to the anchor 614. In various embodiments, the length $l_6$ of the first monopolar branch 611, from its proximal end where it exits the distal end of the bifurcation sleeve 609 to its distal end where it meets the proximal end of the anchor 613, is in a range of 50 mm to 120 mm. In one embodiment, the length $l_6$ of the first monopolar branch 611, from its proximal end where it exits the distal end of the bifurcation sleeve 609 to its distal end where it meets the proximal end of the anchor 613, is 70 mm. In various embodiments, the length $l_7$ of the second monopolar branch 612, from its proximal end where it exits the distal end of the bifurcation sleeve 609 to its distal end where it meets the proximal end of the anchor 614, is in a range of 50 mm to 120 mm. In one embodiment, the length $l_7$ of the second monopolar branch 612, from its proximal end where it exits the distal end of the bifurcation sleeve 609 to its distal end where it meets the proximal end of the anchor 614, is 60 mm.

In various embodiments, the length of the electrodes 615, 616 is in a range of 1 mm to 10 mm. In one embodiment, the length of the electrodes 615, 616 is 5 mm. The different lengths of the first and second monopolar branches allow the electrodes to be positioned in a staggered, in-line configuration. In various embodiments, after anchoring, the electrodes are positioned in a range of 1 to 20 mm apart from one another. In one embodiment, after anchoring, the electrodes are positioned 10 mm apart from one another.

A length of suture material 650, having a first end and a second end, joins the two monopolar branches 611, 612. The first end of the length of suture material 650 is attached to the distal end of the first monopolar branch 611, just distal to the electrode 615, and the second end of the length of suture material 650 is attached to the distal end of the second monopolar branch 612, just distal to the electrode 616. The suture material 650 acts as a loop to direct the lead 600 during implantation. In various embodiments, the suture material has a length of 10 to 150 mm. In one embodiment, the suture material has a length of 60 mm. In one embodiment, the suture material 650 is composed of nylon. In various embodiments, the total length of the lead 600 from the proximal end of the IS-1 connector system 607 to the proximal end of the electrode 615 of the first monopolar branch 611 is in a range of 500 mm to 540 mm. In one embodiment, the total length of the lead 600 from the proximal end of the IS-1 connector system 607 to the proximal end of the electrode 615 of the first monopolar branch 611 is 520 mm.

The implantable electrical implantation lead 600 is designed to be implanted through the working channel of an endoscope. A physician inserts an endoscope into a patient using natural orifice transluminal endoscopic surgery (NOTES). In NOTES, a physician passes an endoscope through a natural orifice in the patient's body, such as, the mouth, urethra, or anus, creates an incision in the wall of an internal organ, such as, the stomach, bladder, or colon, and then passes the endoscope through the incision and into the target area or lumen of the organ. The incision is always internal with a NOTES technique, therefore, no visible scar remains. For the present embodiment, once the distal end of the endoscope is positioned proximate the target anatomy, the physician uses endoscopic graspers to grasp the suture material 650 of the lead 600 and then pulls the lead 600 through the working channel of the endoscope. Alternatively, the lead could be passed through a working channel of a laparoscopic and pulled through the endoscopic tunnel proximate to the target tissue thus eliminating the need to dissect to expose the target tissue. The monopolar branches 611, 612 are then positioned proximate the target anatomy. The anchors 613, 614 are designed to allow for fibrosis around the implantation site in the endoscopic tunnel, thereby holding the electrodes 615, 616 in place and eliminating the need for needles and sutures. In various embodiments, the anchors 613, 614 comprise sleeves having grooves, spikes, or holes to allow for the ingrowth of fibrous tissue and resultant anchoring. In another embodiment, the anchors are narrow plastic strips having a plurality of openings for tissue ingrowth. In another embodiment, the anchors are porous silicone with a plurality of openings for tissue ingrowth and neovascularization. In another embodiment, the anchors are rosette-shaped and include a plurality of openings for tissue ingrowth. In various embodiments, the anchors are configured to be wide enough to perform as stoppers but are sufficiently fluffy (porous) to prevent erosion through the esophageal wall. In one embodiment, the anchors are comprised of silicone. In another embodiment, the anchors 613, 614 are composed of a porous material that promotes fibrosis and anchoring. In one embodiment, the anchors are comprised of a Dacron mesh.

Figure 7:
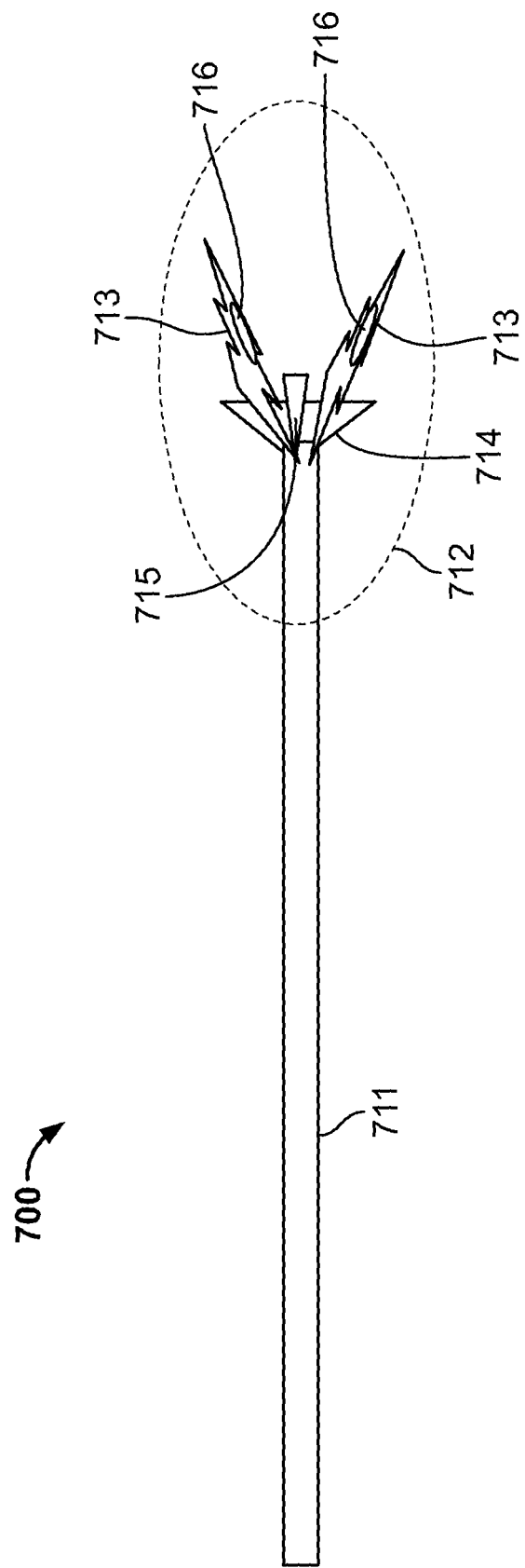
FIG. 7 is a side view illustration of one embodiment of a lead delivery catheter used to implant a needleless electrical stimulation lead using the natural orifice transluminal endoscopic surgery (NOTES) technique; and, FIG. 8 is a flowchart illustrating one embodiment of the steps involved in implanting a needleless electrical stimulation lead using an endoscope.

FIG. 7 is a side view illustration of one embodiment of a lead delivery catheter 700 used to implant the needleless electrical stimulation lead described above using the natural orifice transluminal endoscopic surgery (NOTES) technique. The catheter 700 includes a catheter body 711 having a proximal end, a distal end, and a lumen within. In one embodiment, the catheter 700 has an inflatable balloon 712 attached to its distal end. The inflatable balloon 712 is used to perform blunt dissection during implantation. The catheter 700 also includes a grasping mechanism 713 at its distal end for grasping the lead. In one embodiment, the grasping mechanism 713 comprises a pair of opposing grasping members having teeth for grasping the suture loop of the lead. In one embodiment, the catheter 700 also includes a light source 714 at its distal end for illumination of the implantation area. The light source 714 illuminates the implantation tunnel created using the catheter 700. In one embodiment, the catheter 700 further includes a camera 715 at its distal end for visualization of the implantation area. The light source 714 illuminates the tunnel so that it can be visualized using the camera 715. In one embodiment, the catheter 700 further includes a bipolar electrode 716 for electrocautery of tissues as the implantation site. In one embodiment, the bipolar electrode 716 is incorporated into the grasping mechanism 713. The bipolar electrode 716 is used to create a primary incision, for dissection in the implantation tunnel, and/or for hemostasis during the implantation procedure.

The lead delivery catheter 700 can be used to implant one or more leads via the NOTES technique using an endoscopic approach or a laparoscopic approach. For example, when placing leads proximate the lower esophageal sphincter (LES), an incision is made with the catheter tip in the esophageal wall at least one inch proximal to the LES using an endoscopic approach. Using a laparoscopic approach, an incision is made with the catheter tip in the gastric wall at least one inch distal to the LES. In both approaches, the distal end of the catheter is then advanced through the incision. Air is then pumped through the catheter lumen to inflate the balloon attached to the distal end of the catheter. The inflated balloon is used to create a submucosal or subserosal pocket using blunt dissection. The distal end of the catheter is then further advanced into the pocket and the balloon is deflated and re-inflated to extend the pocket longitudinally, creating a tunnel for the passage of the lead.

In the endoscopic approach, once an adequate tunnel has been created that crosses the implant site, a second incision is made on the contralateral side to create an exit through the gastrointestinal wall. A laparoscopic trocar is inserted into the abdomen with its distal end passing through the second incision. The catheter is advanced further and the lead is passed through the laparoscopic trocar, grasped by the grasping mechanism, and pulled into the created tunnel. The lead is then positioned proximate the LES. In the endoscopic approach, the lead can also be passed through an abdominal incision directly and grasped using the grasping mechanism of the catheter. The lead and the endoscope with the catheter are withdrawn into the tunnel and the lead is released once the electrodes are in the desired position proximate to the LES muscles. In the laparoscopic approach, once an adequate tunnel has been created that crosses the implant site, the catheter is removed from the endoscope. The lead is then passed through a working channel of the endoscope. The catheter is reinserted through a laparoscopic trocar and advanced to the implant site. Using the grasping mechanism, the physician grabs the lead which is then positioned proximate the LES. Over time, fibrosis about the anchors permanently fixes the lead in the tunnel with the stimulating electrodes proximate the LES. In one embodiment, temporary sutures or clips are used to provide temporary anchoring support while fibrosis is setting in about the anchors. The temporary sutures or clips are later removed after permanent anchoring has been achieved with the lead anchors.

Optionally, in another embodiment, the lead is delivered to the implantation site using a laparoscopic method with tunneling from the outside inwards. This implantation is performed completely laparoscopically without the need for an opening at the distal end of the implantation tunnel. The physician laparoscopically creates a dead-end tunnel proximate the target tissues. The lead is then pushed into the blind tunnel and allowed to anchor over time.

Optionally, in another embodiment, the lead is delivered to the implantation site via a completely endoscopic procedure. Using an endoscope and the lead delivery catheter, the physician creates a tunnel as described above. The lead is passed through the endoscope and placed into position using the grasping mechanism of the catheter.

Figure 8:
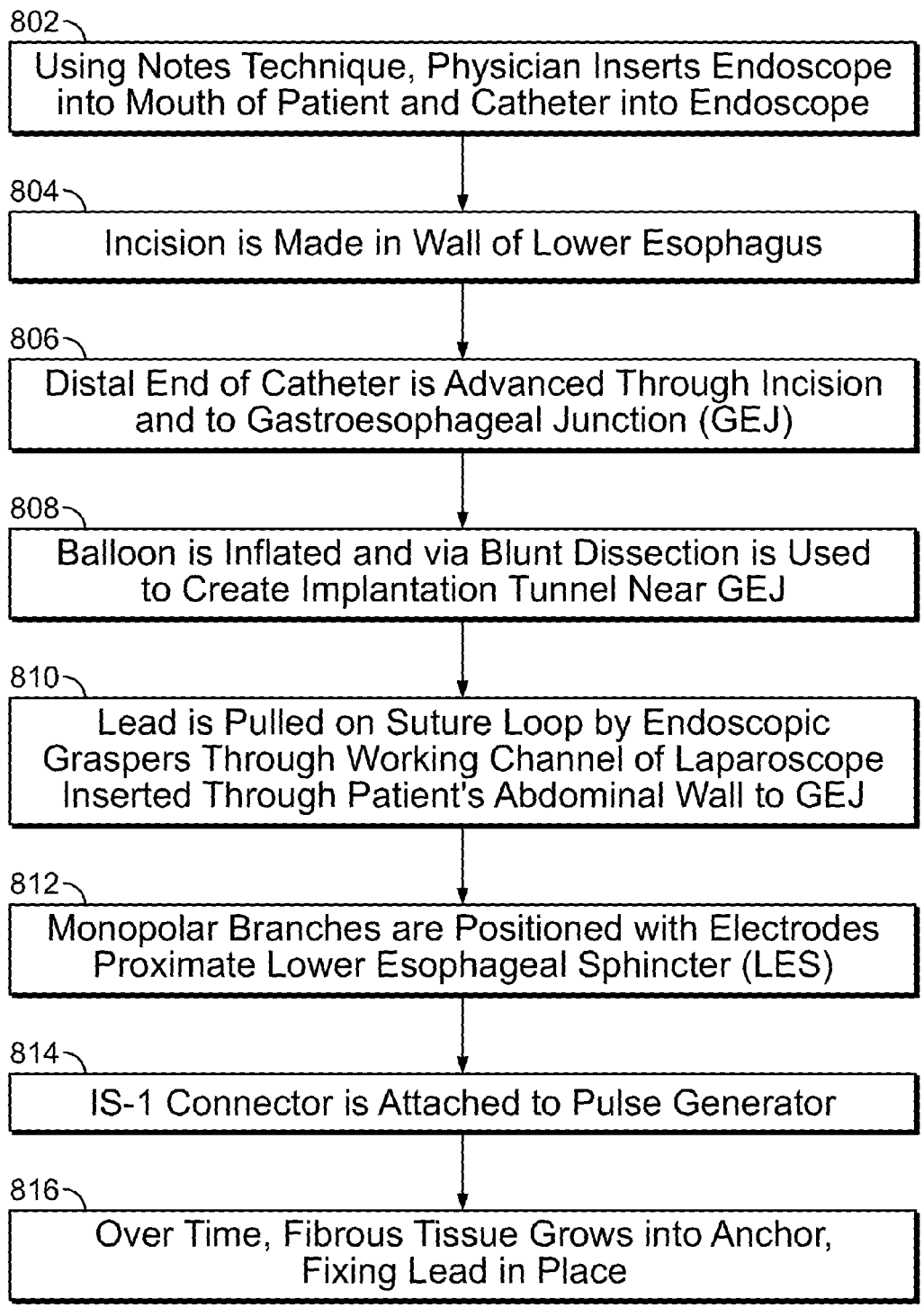

FIG. 8 is a flowchart illustrating one embodiment of the steps involved in implanting the needleless electrical stimulation lead using an endoscope. The lead is of the type having the suture material loop as described with reference to FIG. 6 above. At step 802, using the NOTES technique, a physician inserts an endoscope into the mouth of a patient with lower esophageal sphincter (LES) dysfunction. A lead delivery catheter as described with reference to FIG. 7 is also inserted into a working channel of the endoscope. At step 804, an incision is made in the wall of the lower esophagus. The distal end of the catheter is then advanced through the incision and into an area proximate the GEJ at step 806. At step 808, the balloon at the distal end of the catheter is inflated and used to create an implantation tunnel using blunt dissection. Then, at step 810, the lead is pulled by endoscopic graspers through a laparoscope that has been inserted into the patient's abdomen to the tunnel created proximate the GEJ. The monopolar branches of the lead are then positioned with the electrodes proximate the LES at step 812. At step 814, the IS-1 connector at the other end of the lead is attached to a pulse generator. Over time, at step 816, fibrous tissue grows into the anchor, fixing the lead in place.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. A lead delivery catheter to be used with an endoscope or a laparoscope and for implanting an electrical stimulation lead in a patient, said catheter comprising:
   a catheter body having a proximal end, a distal end, and a lumen within;
   an inflatable balloon attached to said distal end of said catheter body;
   a grasping mechanism comprising a pair of opposing grasping members, each of said grasping members having a plurality of teeth, wherein said grasping mechanism is attached to said distal end of said catheter body for grasping said lead;
   a bipolar electrocautery electrode positioned on said grasping mechanism; and
   an electrical stimulation lead for use in the stimulation of biological tissues comprising:
      an elongate lead body having a proximal end and a distal end, said lead body comprising an electrically conductive inner coil, an electrically conductive outer coil, a first insulating sheath covering said electrically conductive inner coil, and a second insulating sheath covering said electrically conductive outer coil;
      a connector attached to and in electrical communication with said proximal end of said lead body;
      a first elongate branch having a proximal end and a distal end, said first elongate branch comprising said electrically conductive inner coil and said first insulating sheath covering said electrically conductive inner coil and not comprising said electrically conductive outer coil and said second insulating sheath; and
      a second elongate branch having a proximal end and a distal end, said second elongate branch comprising said electrically conductive outer coil and said second insulating sheath covering said electrically conductive outer coil and not comprising said electrically conductive inner coil and said first insulating sheath, wherein said proximal end of said first branch and said proximal end of said second branch join to form said distal end of said lead body, wherein said first insulating sheath extends over a proximal portion of a first electrode and said second insulating sheath extends over a proximal portion of a second electrode such that, after said lead is implanted, said insulating sheaths are configured to be pulled partially in a proximal direction to expose said proximal portions of said first and second electrodes.

2. The lead delivery catheter of claim 1 further comprising a light source adapted to provide illumination and positioned at the distal end.

3. The lead delivery catheter of claim 1 further comprising a camera positioned at the distal end.

4. The lead delivery catheter of claim 1 wherein said lead body has a length within a range of 390 mm to 490 mm.

5. The lead delivery catheter of claim 1 wherein said first branch has a length within a range of 50 mm to 120 mm.

6. The lead delivery catheter of claim 1 wherein said second branch has a length within a range of 50 mm to 120 mm.

7. The lead delivery catheter of claim 1 further comprising a first anchoring element.

8. The lead delivery catheter of claim 1 further comprising a second anchoring element.

9. The lead delivery catheter of claim 1 further comprising a first length of suturing material and a second length of suturing material, each having a proximal end and a distal end, wherein said proximal end of said first length of said suturing material is attached to said distal end of said first branch and said proximal end of said second length of said suturing material is attached to said distal end of said second branch.

10. The lead delivery catheter of claim 9, wherein said first and second lengths of suturing material are each in a range of 55 to 65 mm.

11. The lead delivery catheter of claim 9 further comprising a first needle attached to said distal end of said first length of suturing material and a second needle attached to said distal end of said second length of suturing material, wherein said first needle and said first length of suturing material are used to suture a first anchoring element to a biological tissue and said second needle and said second length of suturing material are used to suture a second anchoring element to a biological tissue.

12. The lead delivery catheter of claim 11 wherein said first and second needles are each within a range of ¼ to ⅜ of a circle curve needles with a length ranging from 18 to 23 mm and include a base having a diameter in a range of 0.68 mm to 0.78 mm.

13. The lead delivery catheter of claim 1 further comprising a sleeve covering the distal end of said lead body and the proximal ends of said first branch and said second branch.

14. The lead delivery catheter of claim 1 further comprising a marking element on said first branch to serve as a visual indicator.

15. A lead delivery catheter to be used with an endoscope or a laparoscope and for implanting an electrical stimulation lead in a patient, said catheter comprising:
- a catheter body having a proximal end, a distal end, and a lumen within;
- an inflatable balloon attached to said distal end of said catheter body;
- a grasping mechanism comprising a pair of opposing grasping members, each of said grasping members having a plurality of teeth, wherein said grasping mechanism is attached to said distal end of said catheter body for grasping said lead;
- a bipolar electrocautery electrode positioned on said grasping mechanism; and
- an electrical stimulation lead for use in the stimulation of biological tissues, said lead comprising:
  - an elongate lead body having a proximal end and a distal end, said lead body comprising an electrically conductive inner coil, an electrically conductive outer coil, a first insulating sheath covering said electrically conductive inner coil, and a second insulating sheath covering said electrically conductive outer coil;
  - a connector attached to and in electrical communication with said proximal end of said lead body;
  - a first elongate branch having a proximal end and a distal end, said first elongate branch comprising said electrically conductive inner coil and said first insulating sheath covering said electrically conductive inner coil and not comprising said electrically conductive outer coil and said second insulating sheath;
  - a second elongate branch having a proximal end and a distal end, said second elongate branch comprising said electrically conductive outer coil and said second insulating sheath covering said electrically conductive outer coil and not comprising said electrically conductive inner coil and said first insulating sheath, wherein said proximal end of said first branch and said proximal end of said second branch join to form said distal end of said lead body; and
  - an additional electrically conductive coil having a proximal end and a distal end, wherein the proximal end of the additional electrically conductive coil is attached to a distal end of the outer coil, wherein a second anchoring element and an electrode are attached to the distal end of the additional electrically conductive coil and wherein the second insulating sheath extends over said additional electrically conductive coil.

* * * * *